(12) United States Patent
Noureldin et al.

(10) Patent No.: US 9,845,995 B2
(45) Date of Patent: Dec. 19, 2017

(54) RECOVERY AND RE-USE OF WASTE ENERGY IN INDUSTRIAL FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/242,041

(22) Filed: Aug. 19, 2016

(65) Prior Publication Data

US 2017/0082374 A1 Mar. 23, 2017

Related U.S. Application Data

(60) Provisional application No. 62/209,217, filed on Aug. 24, 2015, provisional application No. 62/209,147, (Continued)

(51) Int. Cl.
F28D 7/00 (2006.01)
C10G 45/02 (2006.01)
(Continued)

(52) U.S. Cl.
CPC ............ *F28D 7/0083* (2013.01); *B01D 3/007* (2013.01); *B01D 3/32* (2013.01); *B01D 51/10* (2013.01);
(Continued)

(58) Field of Classification Search
CPC .......... F28D 7/0083; F01K 25/06; F28F 9/26; B01D 3/007; B01D 3/32; B01D 51/10; B01D 53/047; B01D 53/1462
See application file for complete search history.

(56) References Cited

U.S. PATENT DOCUMENTS 3,995,428 A 12/1976 Roberts
4,109,469 A 8/1978 Carson
(Continued)

FOREIGN PATENT DOCUMENTS

CN 1844325 10/2006
CN 101424453 A 5/2009
(Continued)

OTHER PUBLICATIONS

Feng Xu, D. Yogi Goswami and Sunil S. Bhagwat, "A combined power/cooling cycle," Energy, 25 (2000), 233-246.
(Continued)

*Primary Examiner* — Brian McCaig
(74) *Attorney, Agent, or Firm* — Fish & Richardson P.C.

(57) ABSTRACT

Configurations and related processing schemes of direct or indirect (or both) intra-plants and thermally coupled heating systems synthesized for grassroots medium grade crude oil semi-conversion refineries to increase energy efficiency from specific portions of low grade waste heat sources are described. Configurations and related processing schemes of direct or indirect (or both) intra-plants and thermally coupled heating systems synthesized for integrated medium grade crude oil semi-conversion refineries and aromatics complex for increasing energy efficiency from specific portions of low grade waste sources are also described.

18 Claims, 20 Drawing Sheets

Related U.S. Application Data filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| F28F 9/26 | (2006.01) | |
| C10G 45/44 | (2006.01) | |
| C10G 35/04 | (2006.01) | |
| B01D 3/32 | (2006.01) | |
| B01D 53/047 | (2006.01) | |
| C10L 3/10 | (2006.01) | |
| C07C 7/08 | (2006.01) | |
| C10G 65/12 | (2006.01) | |
| C10G 33/06 | (2006.01) | |
| B01D 3/00 | (2006.01) | |
| B01D 51/10 | (2006.01) | |
| B01D 53/14 | (2006.01) | |
| B01D 53/18 | (2006.01) | |
| B01D 53/34 | (2006.01) | |
| B01D 53/48 | (2006.01) | |
| B01D 53/86 | (2006.01) | |
| B01D 53/96 | (2006.01) | |
| C02F 1/58 | (2006.01) | |
| C10G 47/00 | (2006.01) | |
| C10G 65/00 | (2006.01) | |
| F01D 17/14 | (2006.01) | |
| F01K 3/18 | (2006.01) | |
| F01K 13/02 | (2006.01) | |
| H02K 7/18 | (2006.01) | |
| C10G 69/00 | (2006.01) | |
| F01K 25/06 | (2006.01) | |
| F01K 25/08 | (2006.01) | |
| F01K 27/02 | (2006.01) | |
| F01K 13/00 | (2006.01) | |
| F01K 23/06 | (2006.01) | |
| C01B 3/24 | (2006.01) | |
| C10G 45/00 | (2006.01) | |
| C10K 3/04 | (2006.01) | |
| F01K 27/00 | (2006.01) | |
| C02F 101/10 | (2006.01) | |
| C02F 101/16 | (2006.01) | |
| C02F 103/18 | (2006.01) | |
| C02F 103/36 | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0233* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11)

(56) References Cited

U.S. PATENT DOCUMENTS

| | | |
|---|---|---|
| 4,291,232 A | 9/1981 | Cardone |
| 4,471,619 A | 9/1984 | Nolley, Jr. |
| 4,512,155 A | 4/1985 | Sheinbaum |
| 4,792,390 A | 12/1988 | Staggs |
| 4,962,238 A | 10/1990 | Wolfe |
| 5,007,240 A | 4/1991 | Ishida |
| 5,164,070 A | 11/1992 | Munro |
| 5,240,476 A | 8/1993 | Hegarty |
| 5,497,624 A | 3/1996 | Amir |
| 6,733,636 B1 | 5/2004 | Heins |
| 8,046,999 B2 | 11/2011 | Doty |
| 9,328,634 B2 | 5/2016 | Ikegami |
| 9,562,201 B2 | 2/2017 | Noureldin |
| 2002/0023538 A1 | 2/2002 | Agarwal |
| 2003/0092952 A1 | 5/2003 | Netzer |
| 2003/0132138 A1 | 7/2003 | Mehra |
| 2004/0186332 A1 | 9/2004 | Kong |
| 2006/0010872 A1 | 1/2006 | Singh |
| 2008/0128134 A1 | 6/2008 | Mudunuri |
| 2008/0174115 A1 | 7/2008 | Lambirth |
| 2008/0257413 A1 | 10/2008 | Noureldin et al. |
| 2008/0289588 A1 | 11/2008 | Wees et al. |
| 2008/0314726 A1 | 12/2008 | Choros |
| 2009/0000299 A1 | 1/2009 | Ast |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2011/0016863 A1 | 1/2011 | Ernst |
| 2011/0072819 A1 | 3/2011 | Silva |
| 2011/0072820 A1 | 3/2011 | Finkenrath |
| 2011/0083437 A1 | 4/2011 | Ast |
| 2011/0158858 A1 | 6/2011 | Alves |
| 2012/0031096 A1 | 2/2012 | Acikgoz et al. |
| 2012/0047889 A1 | 3/2012 | Acikgoz et al. |
| 2012/0048718 A1* | 3/2012 | Werba .......... B01D 3/007 203/26 |
| 2012/0085096 A1 | 4/2012 | Penton et al. |
| 2012/0131921 A1 | 5/2012 | Held |
| 2012/0279728 A1 | 11/2012 | Northrop |
| 2012/0279900 A1 | 11/2012 | Noureldin et al. |
| 2012/0285169 A1 | 11/2012 | Freund |
| 2012/0298552 A1 | 11/2012 | Koseoglu |
| 2013/0104546 A1 | 5/2013 | Goswami |
| 2013/0145763 A1 | 6/2013 | Mirmobin et al. |
| 2013/0165534 A1 | 6/2013 | McComish |
| 2013/0213040 A1 | 8/2013 | Goswami |
| 2013/0231909 A1 | 9/2013 | Noureldin |
| 2013/0238154 A1 | 9/2013 | Noureldin |
| 2013/0334060 A1 | 12/2013 | Koseoglu et al. |
| 2014/0090405 A1 | 4/2014 | Held et al. |
| 2014/0142364 A1 | 5/2014 | Io |
| 2014/0260311 A1 | 9/2014 | Berlowitz |

(56) References Cited

U.S. PATENT DOCUMENTS

| | | |
|---|---|---|
| 2015/0377079 A1 | 12/2015 | Noureldin |
| 2016/0045841 A1 | 2/2016 | Kaplan |

FOREIGN PATENT DOCUMENTS

| | | |
|---|---|---|
| CN | 104560082 A | 4/2015 |
| DE | 3731978 | 3/1988 |
| EP | 0292391 | 11/1988 |
| EP | 949318 | 10/1999 |
| EP | 2516326 | 10/2012 |
| FR | 2990990 | 11/2013 |
| SU | 295317 | 10/1977 |
| WO | 97/21786 | 6/1997 |
| WO | 2004102082 | 11/2004 |
| WO | 2011090553 | 7/2011 |
| WO | 2012048132 | 4/2012 |
| WO | 2013055864 | 4/2013 |
| WO | 2014205163 | 12/2014 |

OTHER PUBLICATIONS

D. Zheng, B. Chen, Y. Qi and H. Jin, "Thermodynamic analysis of a novel absorption power/cooling combined cycle," Applied Energy, 83 (2006), 311-323.
Meng Liu, and Na Zhang, "Proposal and analysis of a novel ammonia-water cycle for power and refrigeration cogeneration," Energy, 32 (2007), 961-970.
J.Wang, Y. Dai and L. Gao, "Parametric analysis and optimization for a combined power and refrigeration cycle" Applied Energy, 85 (2008), 1071-1085.
R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.
D. Ayou, J. C. Bruno, R. Saravanan and A. Coronas, "An Overview of Combined Absorption Power and Cooling Cycles," Renewable sustainable energy reviews, 21 (2013), 728-748.
J. Hua, Y. Chen, Y. Wang and A.P. Roskilly, "Thermodynamic analysis of ammonia-water power/chilling cogeneration cycle with low grade waste heat," Applied thermal engineering, 64 (2014), 483-490.
Hasan et al., "First and Second Law Analysis of a New Power and Refrigeration Thermodynamic Cycle using a Solar Heat Source," Pergarnon, Solar Energy, vol. 73, No. 5, Nov. 1, 2002, pp. 385-393.
Stecco, "Kalina Cycles: Some Possible Applications and Comments," Proceedings of the American Power Conference, XP 000609703, Jan. 1, 1993, vol. 1, pp. 196-201.
Tamm et al., "Theoretical and Experimental Investigation of an Ammonia-Water Power and Refrigeration Thermodynamic Cycle," Science Direct, Solar Energy, vol. 76, No, 1-3, Jan. 1, 2004, pp. 217-228.
Sadrameli et al., "Optimum Operating Conditions for a Combined Power and Cooling Thermodynamic Cycle," Science Direct, Applied Energy, vol. 84, No. 3, Nov. 10, 2006, pp. 254-265.
Vidal, "Analysis of a Combined Power and Refrigeration Cycle by the Exergy Method," Science Direct, Energy 31, Dec. 1, 2006, pp. 3401-3414.
PCT International Search Report and Written Opinion of the International Searching Authority, PCT/US2016/027417, dated Jul. 6, 2016, 11 pages.
PCT International Search Report and Written Opinion of the International Searching Authority, PCT/US2016/027797, dated Oct. 19, 2016, 12 pages.
PCT International Search Report and Written Opinion of the International Searching Authority, FCT/US2016/027794, dated Oct. 19, 2016, 13 pages.
PCT International Search Report and Written Opinion of the International Searching Authority, PCT/US2016/030063, dated Oct. 19, 2016, 13 pages.
PCT International Search Report and Written Opinion of the International Searching Authority, PCT/US2016/030156, dated Oct. 19, 2016, 12 pages.
PCT International Search Report and Written Opinion of the International Searching Authority, PCT/US2016/048074, dated Nov. 9, 2016, 12 pages.
PCT International Search Report and Written Opinion of the International Searching Authority, PCT/US2016/048042, dated Nov. 9, 2016, 12 pages.
PCT International Search Report and Written Opinion of the International Searching Authority, PCT/US2016/048066, dated Nov. 15, 2016, 11 pages.
PCT International Search Report and Written Opinion of the International Searching Authority, PCT/US2016/048078, dated Nov. 15, 2016, 12 pages.
PCT International Search Report and Written Opinion of the International Searching Authority, PCT/US2016/048076, dated Nov. 15, 2016, 12 pages.
PCT International Search Report and Written Opinion of the International Searching Authority, PCT/US2016/048207, dated Nov. 21, 2016, 12 pages.
PCT International Search Report and Written Opinion of the International Searching Authority, PCT/US2016/048219, dated Nov. 21, 2016, 13 pages.
PCT International Search Report and Written Opinion of the International Searching Authority, PCT/US2016/048229, dated Nov. 21, 2016, 13 pages.
PCT International Search Report and Written Opinion of the International Searching Authority, PCT/US2016/048236, dated Nov. 21, 2016, 13 pages.
PCT International Search Report and Written Opinion of the International Searching Authority, PCT/US2016/048210, dated Dec. 22, 2016, 11 pages.
PCT International Search Report and Written Opinion of the International Searching Authority, PCT/US2016/048224, dated Dec. 22, 2016, 11 pages.
PCT International Search Report and Written Opinion of the International Searching Authority, PCT/US2016/048209, dated Dec. 22, 2016, 11 pages.
PCT International Search Report and Written Opinion of the International Searching Authority, PCT/US2016/048237, dated Dec. 22, 2016, 11 pages.
PCT International Search Report and Written Opinion of the International Searching Authority, PCT/US2016/048223, dated Dec. 22, 2016, 11 pages.
PCT International Search Report and Written Opinion of the International Searching Authority, PCT/US2016/048212, dated Dec. 22, 2016, 11 pages.
PCT International Search Report and Written Opinion of the International Searching Authority, PCT/US2016/048067, dated Nov. 15, 2016, 11 pages.
PCT International Search Report and Written Opinion of the International Searching Authority, PCT/US2016/027413, dated Nov. 22, 2016, 11 pages.
PCT International Search Report and Written Opinion of the International Searching Authority, PCT/US2016/048063, dated Nov. 23, 2016, 11 pages.
PCT International Search Report and Written Opinion of the International Searching Authority, PCT/US2016/048071, dated Nov. 23, 2016, 11 pages.
Schaschke, "A Dictionary of Chemical Engineering: Tatoray Process," Oxford, 2014, p. 371.
Marcilly, "Acido-Basic Catalysis: Applications to refining and Petrochemistry," IFP Publications, 2005, pp. 512-513.
Gary, "Petroleum Refining Technology and Economics: Figure 1.1 Refinery Flow Diagram," CRC Press, 5th ed., 2007, p. 3.

\* cited by examiner

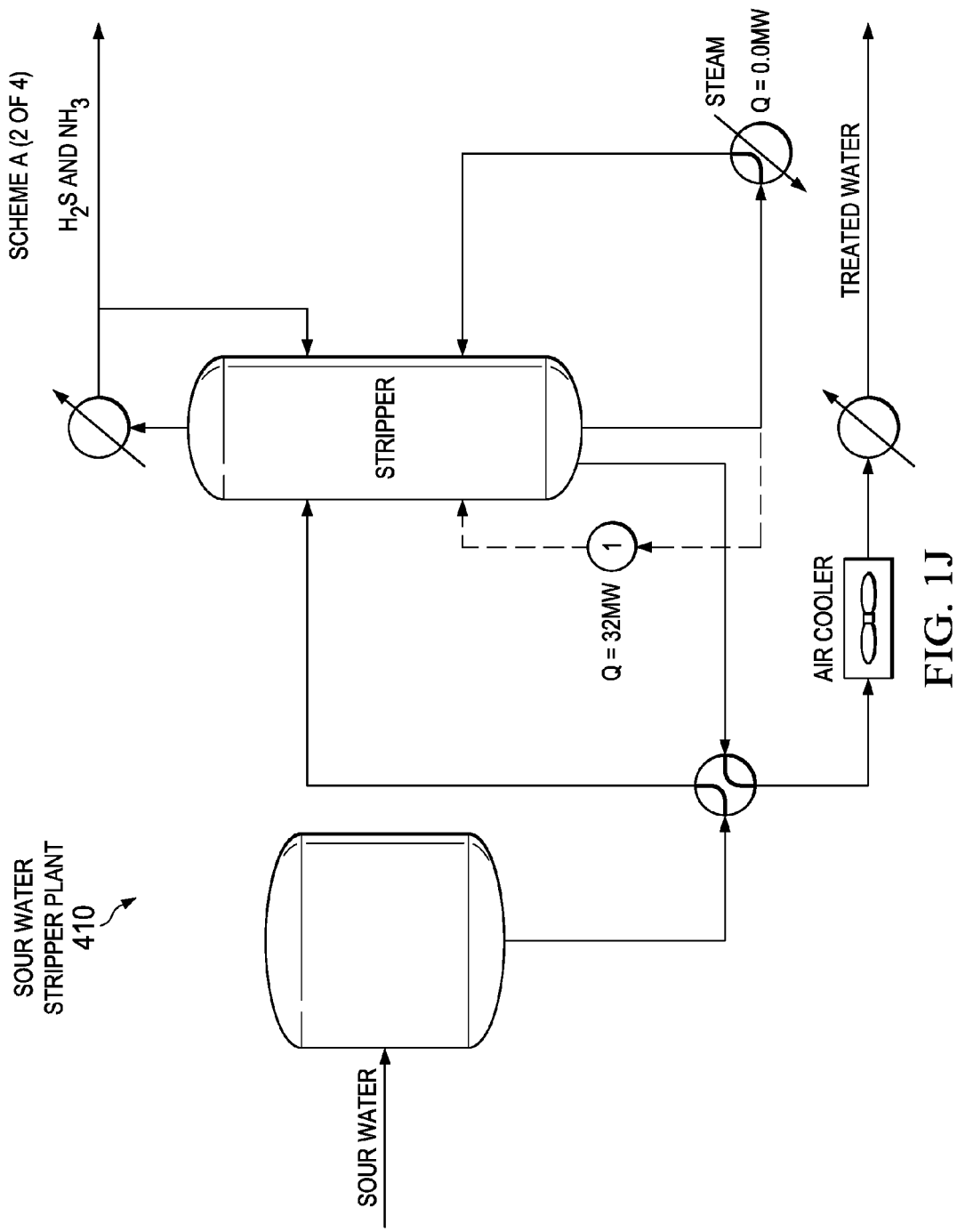

RECOVERY AND RE-USE OF WASTE ENERGY IN INDUSTRIAL FACILITIES

CROSS-REFERENCE TO RELATED APPLICATIONS

This application claims priority under 35 U.S.C. §119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to intra-plants waste heat recovery schemes and plants' thermal coupling for integrated refining-petrochemical facilities' thermal energy consumption reduction from waste energy in industrial facilities.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIG. 1A is a schematic diagram of an aromatics complex xylene products separation unit.

FIG. 1J is a schematic diagram of a sour water stripper plant.

FIG. 1QB is a schematic diagram of an amine regeneration plant separation section.

FIG. 1RA is a schematic diagram of an aromatics complex xylene products separation unit.

FIG. 1RB is a schematic diagram of an amine regeneration plant separation section.

DETAILED DESCRIPTION

Figure 1A:
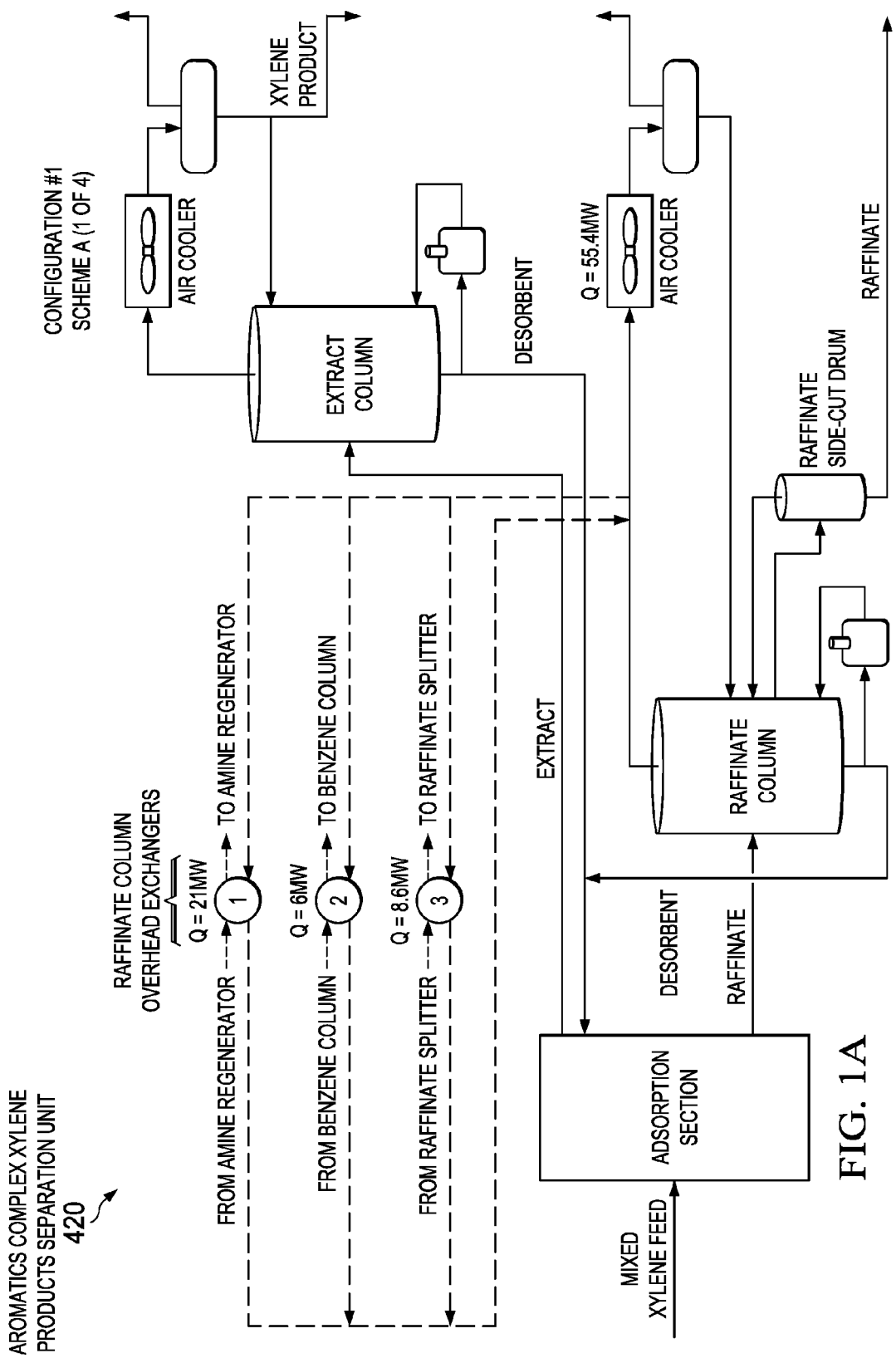
FIGS. 1A-1R (consisting of 1RA and 1RB) illustrate configurations and related scheme details for thermally integrating refining sub-units of an aromatics plant in the crude oil refining facility.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM British Thermal Units per hour (Btu/hr) can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydrotreating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3° C. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used in an acid gas absorber and regenerator to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromaticscontent or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromaticsfeedstock is converted into lighter products under a wide range of high pressures and high temperatures in the presence of hydrogen and special catalysts. When the feedstock has a high paraffinic content, hydrogen prevents the formation of polycyclic aromaticscompounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Removal Plant

Sulfur removal facilities in refineries operate to regulate the discharge of sulfur compounds to the atmosphere to meet environmental regulations. In a sulfur removal plant, combustion products that include sulfur can be processed, for example, by heating, cooling with condensers, using sulfur conversion catalyst, and by other processing techniques.

9. Naphtha Hydrotreating Plant and Continuous Catalytic Reformer Plants

A Naphtha Hydrotreater (NHT) produces 101 Research Octane Number (RON) reformate, with a maximum 4.0 psi (pounds per square inch) Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, i.e., the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes new energy efficient configurations and the related specific processing schemes for integrated medium grade semi-conversion crude oil refining facility and aromatics complex through simultaneous intra-plant integration and plants' thermal coupling.

In some implementations, a semi-conversion medium grade crude oil refining facility includes an aromatics complex. This disclosure describes a waste heat recovery and reuse network for such a refining facility. As described later, waste heat can be recovered from one or more of the units in the refining facility. Such a refinery typically consumes several hundred megawatts of energy (for example, about 650 MW) in heating utilities. Implementing the configurations described here can not only reduce energy consumption but also reduce energy-based greenhouse gas (GHG) emissions. In particular, this disclosure describes a method implemented in a crude oil refining facility to heat multiple streams in multiple plants of a crude oil refining facility using one or more streams in one or more aromatics plant sub-units included in an aromatics plant in the crude oil refining facility. Several configurations of process schemes for doing so are described later with reference to the following figures.

Configuration 1

FIGS. 1A-1H illustrate configurations and related scheme details for thermally integrating an aromatics complex sub-unit with other aromatics complex sub-units and a sulfur recovery plant in the crude oil refinery. In certain schemes, a process stream (for example, a stream from one refining sub-unit of an aromatics plant or other process streams) can be used to directly heat another process stream (for example, another stream from another refining sub-unit of the aromatics plant or other process stream). In certain configurations, heat exchange between process streams can be implemented using an intermediate buffer fluid, for example, water, oil, or other buffer fluid.

Configuration 1—Scheme A

FIGS. 1A-1D illustrate configurations and related scheme details for thermally integrating different refining plants in the crude oil refining facility. The thermal integration described in these configurations and illustrated in FIGS. 1A-1D can reduce the crude oil refining facility's energy consumption (for example, heating and cooling utilities). For example, a reduction in energy consumption by about 36 MW (for example, 35.6 MW), which can translate to about 6% of the energy consumption in the crude oil refining facility. As described later, in certain schemes, a process stream (for example, an aromatics complex xylene products unit stream or other process streams) can be used to directly heat another process stream (for example, a sulfur recovery plant stream or other process stream).

In some implementations, multiple first streams in a multiple first plants can be directly heated using a second stream in a single second plant. In some implementations, the multiple first plants can include a sulfur recovery plant and an aromatics complex benzene extraction unit, and the multiple first streams can include an amine regenerator bottoms, a benzene column bottoms, and a raffinate splitter bottoms streams. The second plant can include an aromatics complex xylene products separation unit, and the second stream can include a raffinate column overheads stream.

FIG. 1A shows an aromatics complex xylene products separation unit 420 in a crude oil refinery facility. The raffinate column overheads stream can be flowed in the plant as a single stream and split into multiple streams or it can be flowed into the plant as multiple streams. In some implementations, as shown in FIG. 1A, a raffinate overheads stream is separated into three streams to facilitate heat recovery. A first raffinate column overheads stream directly heats an amine regenerator bottom stream in a first heat exchanger with a thermal duty that can range between about 15 MW and 25 MW (for example, 21 MW). A second raffinate column overheads stream directly heats a benzene column bottoms stream in a second heat exchanger with a thermal duty that can range between about 1 MW and 10 MW (for example, 6 MW). A third raffinate column overheads stream directly heats a raffinate splitter column bottoms stream in a third heat exchanger with a thermal duty that can range between about 5 MW and 15 MW (for example, 8.6 MW). In this manner, the first heat exchanger, the second heat exchanger and the third heat exchanger are coupled to each other in parallel in relation to the flow of the raffinate column overhead stream. For each raffinate column overheads stream, the transfer of heat directly to another process stream captures heat that would have otherwise been discharged to the environment. The raffinate overheads streams are recombined and are returned to the xylene products separation unit 420 for further processing.

Figure 1B:
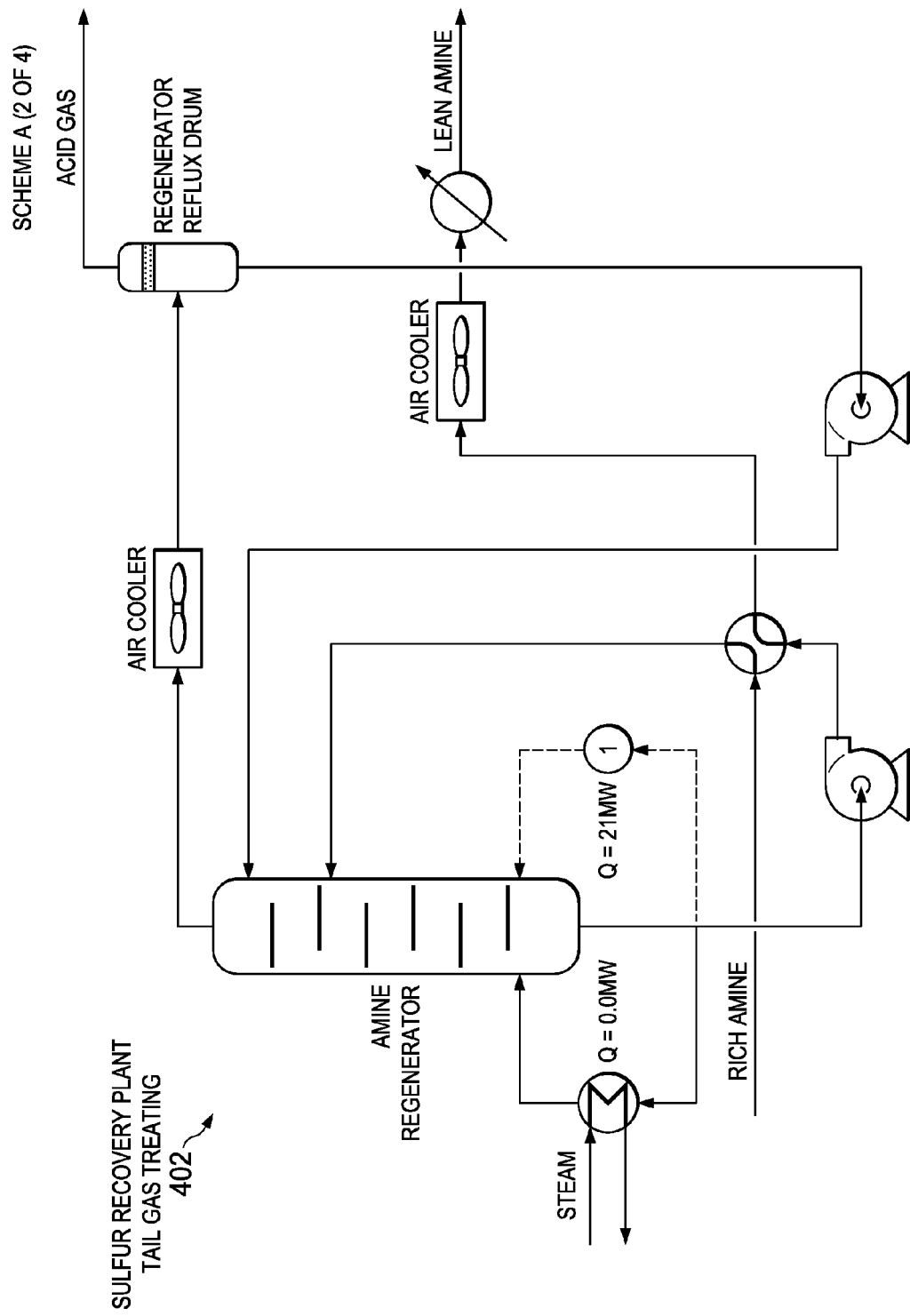
FIG. 1B is a schematic diagram of a sulfur recovery plant tail gas treating unit.

FIG. 1B shows the sulfur recovery plant 402 in a crude oil refinery facility. The heated amine regenerator bottom stream is flowed to the sulfur recovery plant 402. As shown in FIG. 1B, the steam heat input for the amine regenerator can be 0 MW because the alternative flow path disclosed in this configuration may satisfy the entire heat load for the operation of the column. In an alternative embodiment, the steam heat input for the sulfur recovery plant amine regenerator can be reduced because the alternative flow path disclosed in this configuration may partially satisfy the heat load for the operation of the column.

Figure 1C:
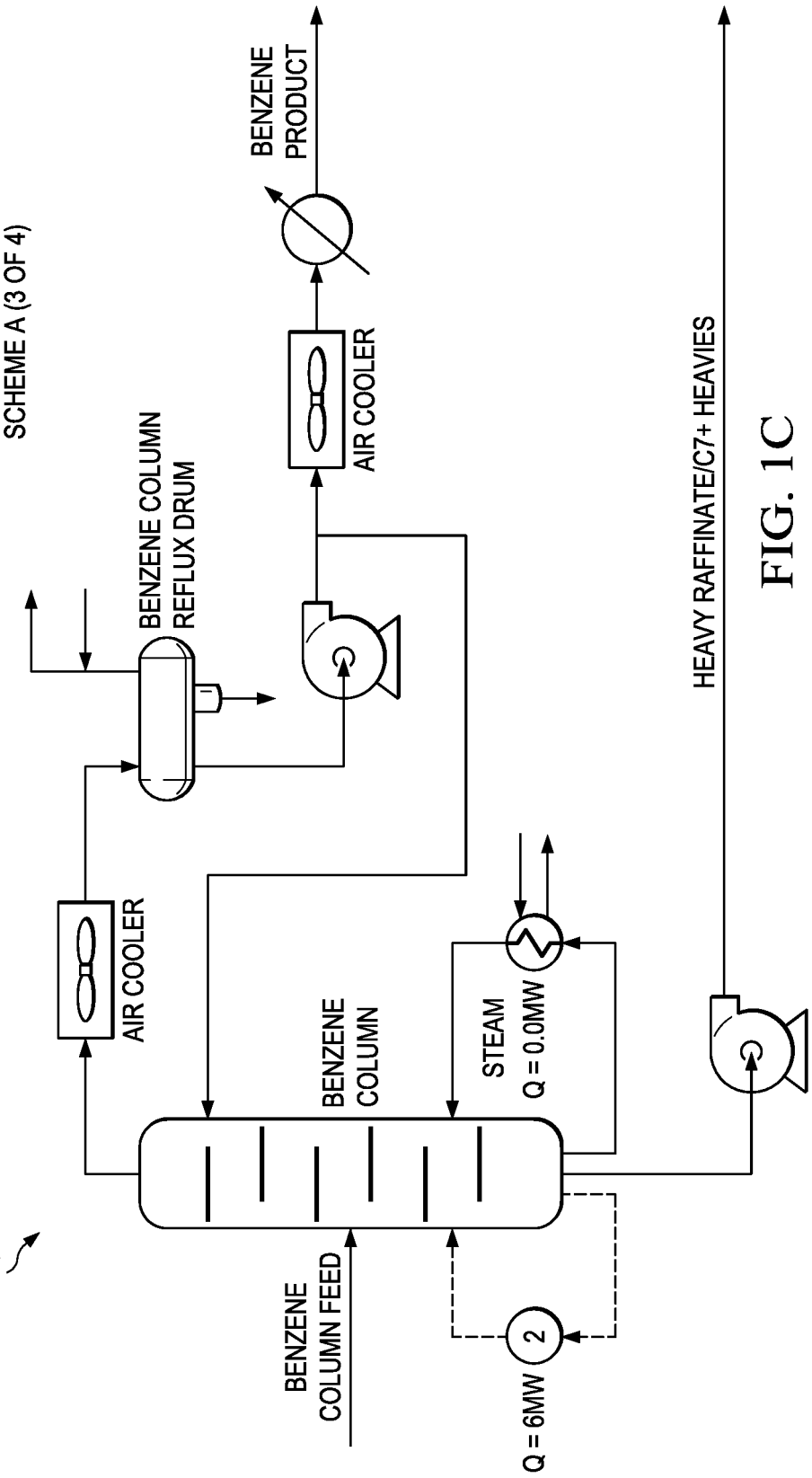
FIG. 1C is a schematic diagram of an aromatics complex xylene products separation unit.

FIG. 1C shows the benzene extraction unit 418 in a crude oil refinery facility. The heated benzene column bottom stream is flowed to the benzene extraction unit 418. As shown in FIG. 1C the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1D:
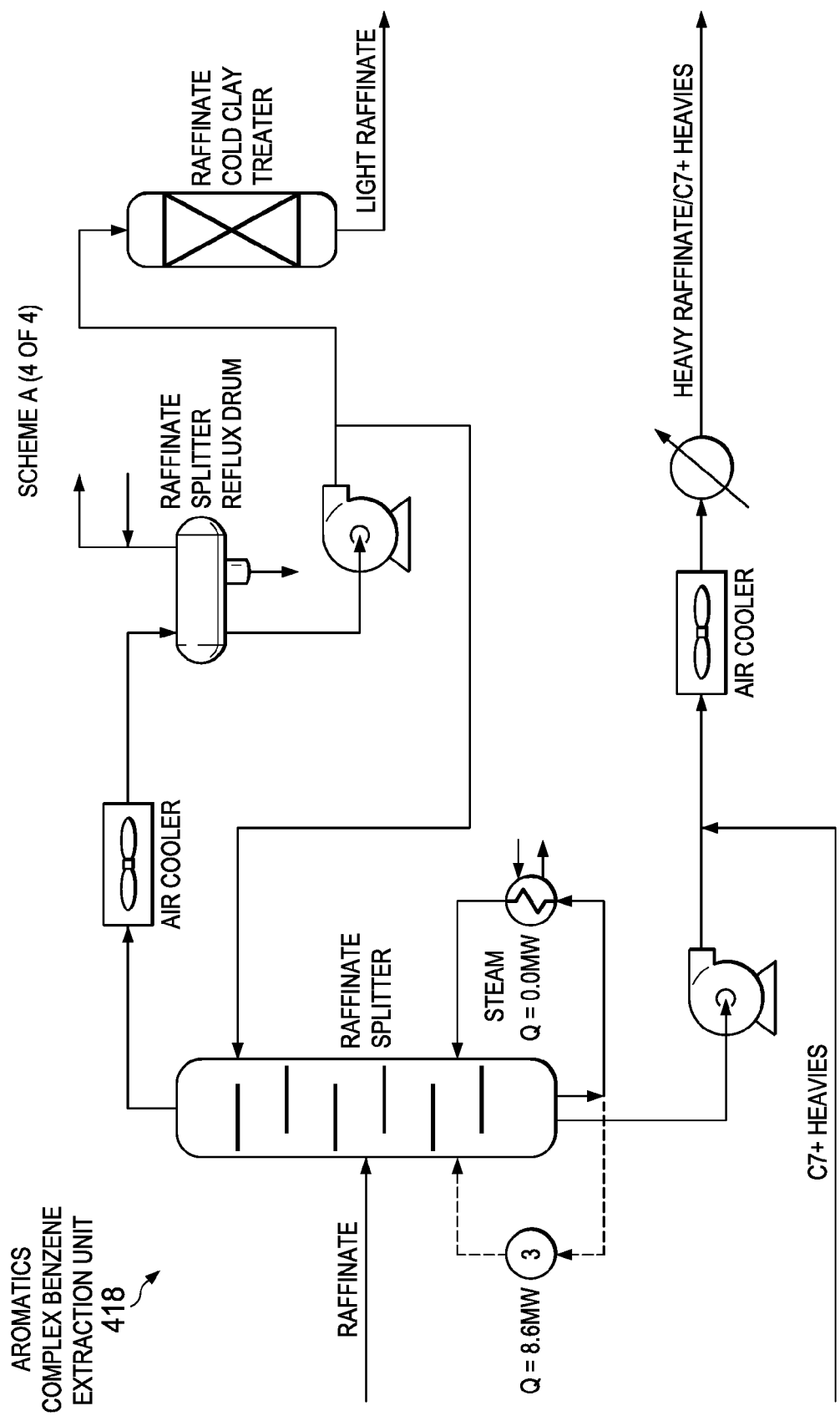
FIG. 1D is a schematic diagram of an aromatics complex xylene products separation unit.

FIG. 1D also shows the benzene extraction unit 418 in a crude oil refinery facility. The heated raffinate splitter column bottom stream is then flowed to the benzene extraction unit 418. As shown in FIG. 1D, the steam heat input for the raffinate splitter column can be 0 MW because the alternative flow path disclosed in this configuration may satisfy the entire heat load for the operation of the column. In an alternative embodiment, the steam heat input for the raffinate splitter column can be reduced because the alternative flow path disclosed in this configuration may partially satisfy the heat load for the operation of the column.

In this manner, the aromatics complex xylene products separation unit directly heats both the sulfur recovery plant and the aromatics complex benzene extraction unit using recovered waste heat, saving about 36 MW of heat energy.

Configuration 1—Scheme B

As shown in FIGS. 1E-1H, in some implementations, multiple first streams in a multiple first plants can be heated indirectly using a second stream in a single second plant. In some implementations, the multiple first plants can include a sulfur recovery plant and an aromatics complex benzene extraction unit, and the second streams can include an amine regenerator bottoms, a benzene column bottoms, and a raffinate splitter bottoms streams. The second plant can include an aromatics complex xylene products separation unit, and the second plant stream can include a raffinate column overheads stream.

The thermal integration described and illustrated in FIGS. 1E-1H can reduce the crude oil refining facility's energy consumption (for example, heating and cooling utilities). For example, a reduction in energy consumption by about 36 MW can translate to about 6% of the energy consumption in the crude oil refining facility. As described later, the heat exchange between process streams can be implemented using an intermediate buffer fluid, for example, water, oil, or other buffer fluid.

Figure 1E:
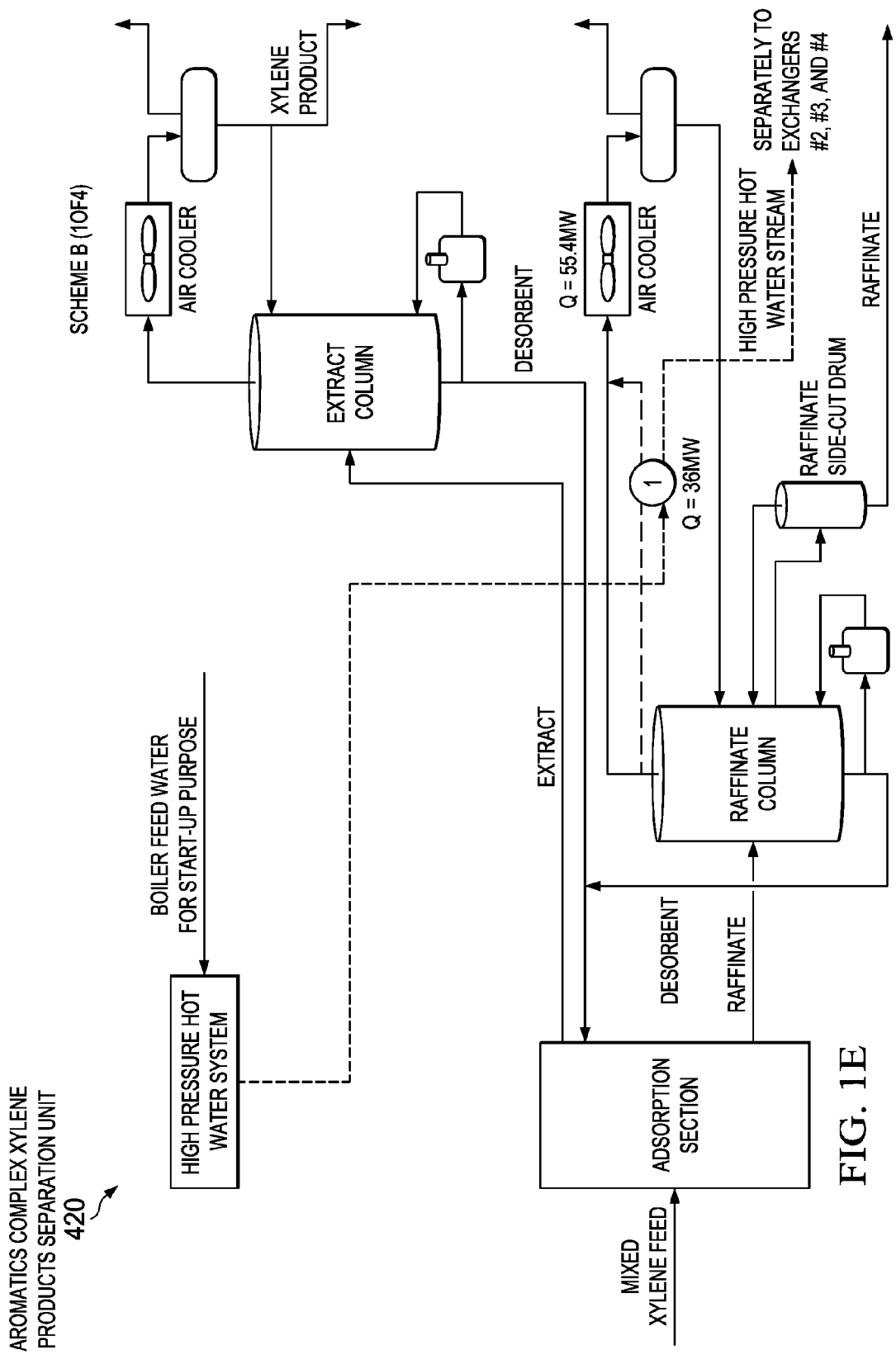
FIG. 1E is a schematic diagram of an aromatics complex xylene products separation unit.

Indirectly heating the streams can include heating the streams through a buffer fluid, for example, oil, water, or other buffer fluid. A buffer fluid (for example, high pressure water) from a buffer fluid tank (for example, hot water tank) is flowed to the aromatics complex xylene products separation unit 420, as shown in FIG. 1E. The buffer fluid can be flowed into a plant as a single stream and split into multiple streams or it can be flowed into a plant as multiple streams.

FIG. 1E shows an aromatics complex xylene products separation unit 420. In some implementations, a buffer fluid from a buffer fluid collection tank is flowed to the aromatics plant xylene products separation unit 420. A raffinate column overheads stream heats the buffer fluid in a first heat exchanger with a thermal duty that can range between about 30 MW and 40 MW (for example, 36 MW). The transfer of heat from the process stream into the buffer fluid captures heat that would have otherwise been discharged to the environment. The raffinate column overheads stream is returned to the xylene products separation unit 420 for further processing.

The heated buffer fluid is flowed to a heated buffer fluid collection header. The heated buffer fluid from the collection header (or in some embodiments, a heated or insulated buffer fluid tank or storage unit that can hold heated collected buffer fluid for a period before use) can be flowed to the sulfur recovery plant 402 or the benzene extraction unit 418. As shown in FIG. 1E, the heated buffer fluid is distributed in three branches to both the sulfur recovery plant 402 and the benzene extraction unit 418.

Figure 1F:
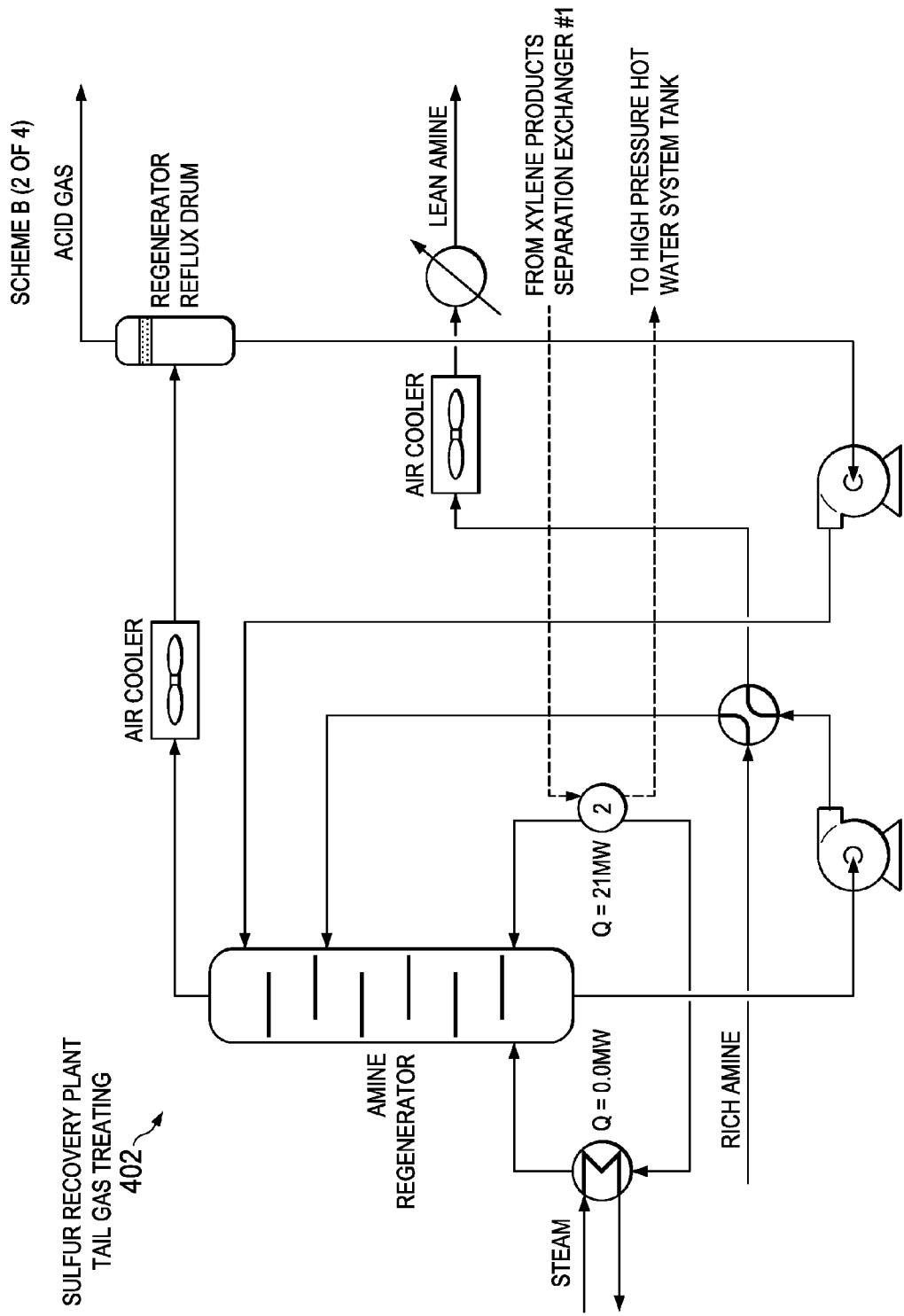
FIG. 1F is a schematic diagram of a sulfur recovery plant tail gas treating unit.

FIG. 1F shows the sulfur recovery plant 402 in a crude oil refinery facility. A first heated buffer fluid stream is flowed to the sulfur recovery plant 402. The first heated buffer fluid stream heats an amine regenerator bottom stream in a second heat exchanger, which has a thermal duty that can range between about 15 MW and 25 MW (for example, 21 MW). The second heat exchanger is coupled in series with and is downstream of the first heat exchanger relative to the flow of heated buffer fluid. As shown in FIG. 1F, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Figure 1G:
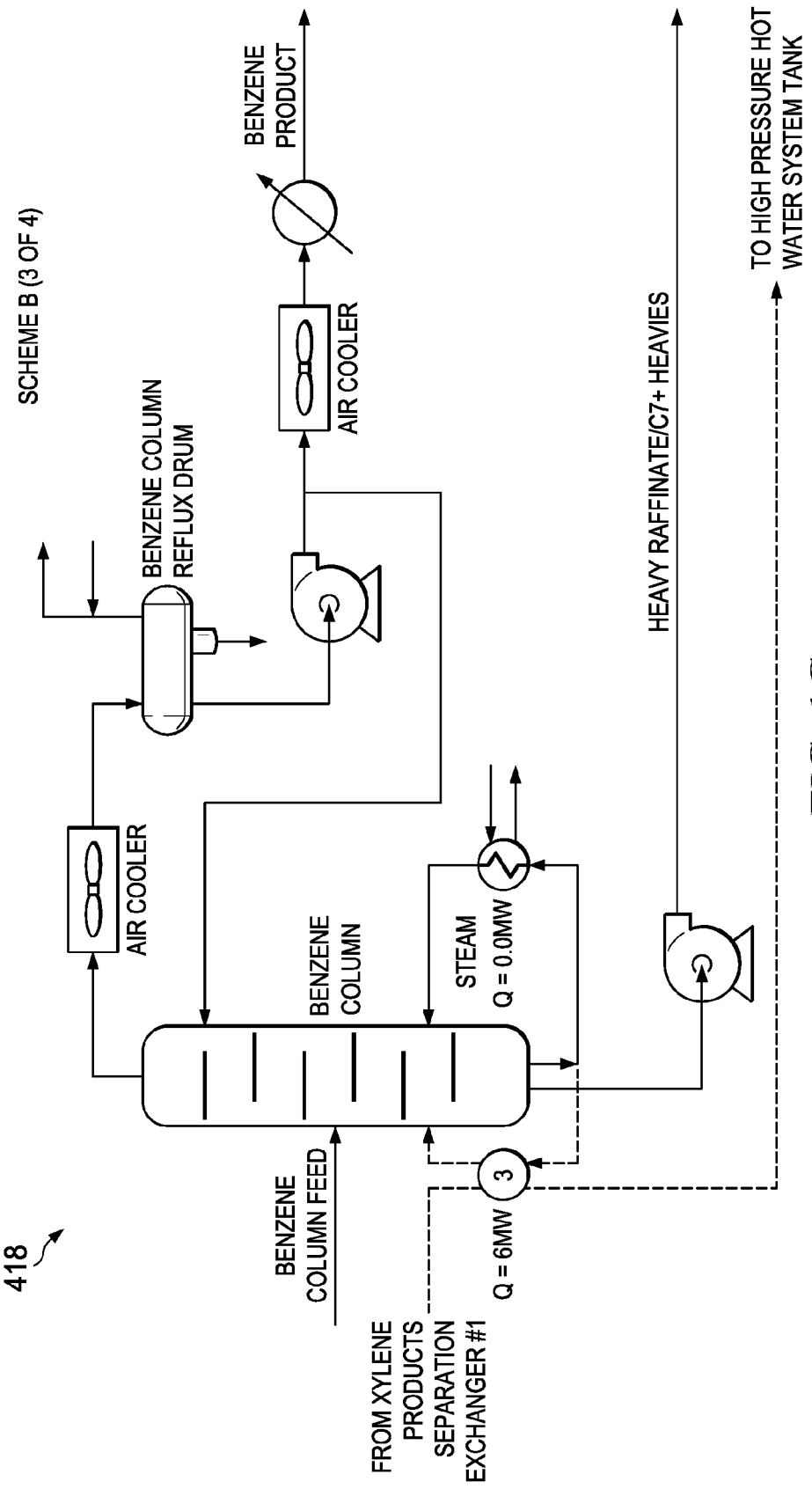
FIG. 1G is a schematic diagram of an aromatics complex benzene products separation unit.

FIG. 1G shows the benzene extraction unit 418 in a crude oil refinery facility. A second heated buffer fluid stream is flowed to the aromatics complex benzene extraction unit 418. The second heated buffer fluid stream heats a benzene column bottom stream in a third heat exchanger, which has a thermal duty that can range between about 1 MW and 10 MW (for example, 6 MW). The third heat exchanger is coupled in series with and is downstream of the first heat exchanger relative to the flow of heated buffer fluid. As shown in FIG. 1G, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1H:
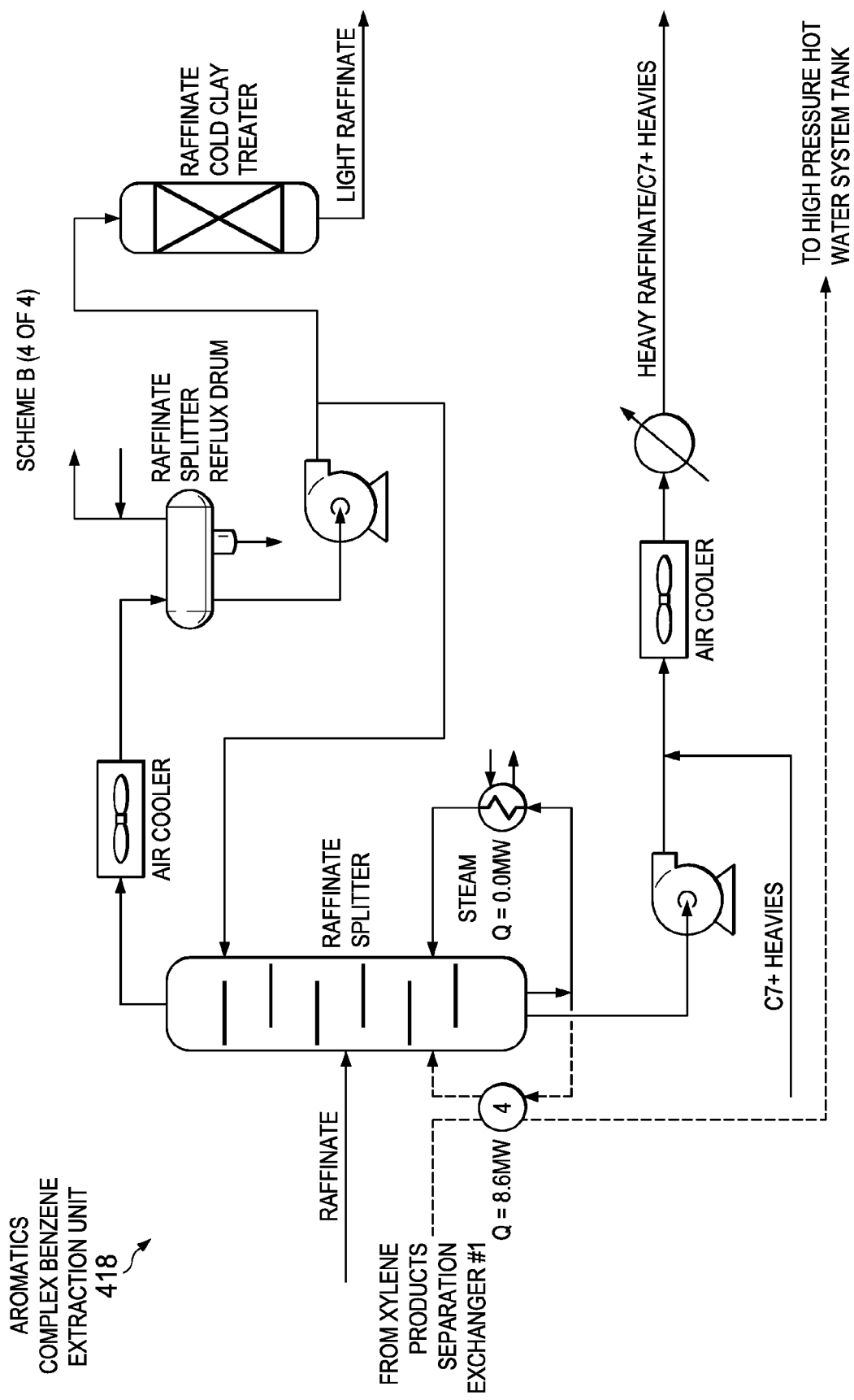
FIG. 1H is a schematic diagram of an aromatics complex benzene products separation unit.

FIG. 1G shows the benzene extraction unit 418 in a crude oil refinery facility. A third heated buffer fluid stream flows to the aromatics complex benzene extraction unit 418. The third heated buffer fluid stream heats a raffinate splitter column bottom stream in a fourth heat exchanger, which has a thermal duty that can range between about 5 MW and 15 MW (for example, 8.6 MW). The fourth heat exchanger is coupled in series with and is downstream of the first heat exchanger relative to the flow of heated buffer fluid. As shown in FIG. 1H, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

The heated buffer fluid exiting the second heat exchanger, the third heat exchangers and the fourth heat exchanger are each flowed to the collection header or the buffer fluid tank. In this manner, the second heat exchanger, the third heat exchangers and the fourth heat exchanger are fluidically coupled to each other in parallel relative to the flow of the heated buffer fluid.

FIGS. 1E-1H show that such recovery and reuse of waste heat indirectly from a first aromatics complex sub-unit can result in decreasing or eliminating the heat energy requirement to heat the streams in both the sulfur recovery plant and a second aromatics complex sub-unit such as by about 36 MW.

Configuration 2

FIGS. 1I-1P illustrate configurations and related scheme details for thermally integrating an aromatics plant sub unit with other aromatics complex sub-units and a sour water stripper plant in the crude oil refining facility. In certain schemes, a process stream (for example, a stream from one refining sub-unit of an aromatics plant or other process streams) can be used to directly heat another process stream (for example, another stream from another refining sub-unit of the aromatics plant or other process stream). In certain configurations, heat exchange between process streams can be implemented using an intermediate buffer fluid, for example, water, oil, or other buffer fluid.

Configuration 2—Scheme A

As shown in FIGS. 1I-1L, different refining plants in the crude oil refining facility are thermally integrated. The thermal integration described in these configurations and illustrated in FIGS. 1I-1L can reduce the crude oil refining facility's energy consumption (for example, heating and cooling utilities). For example, a reduction in energy consumption by about 47 MW can translate to about 7% of the energy consumption in the crude oil refining facility. As described later, in certain schemes, a process stream (for example, an aromatics complex xylene products unit stream or other process streams) can be used to directly heat another process stream (for example, a sour water stripper plant stream or other process stream).

In some implementations, multiple first streams in a multiple first plants can be directly heated using a second stream in a single second plant. In some implementations, the multiple first plants can include a sour water stripper plant and an aromatics complex benzene extraction unit, and the multiple first streams can include a sour water stripper regenerator bottoms, a benzene column bottoms, and a raffinate splitter bottoms streams. The second plant can include an aromatics complex xylene products separation unit, and the second stream can include a raffinate column overheads stream.

Figure 1I:
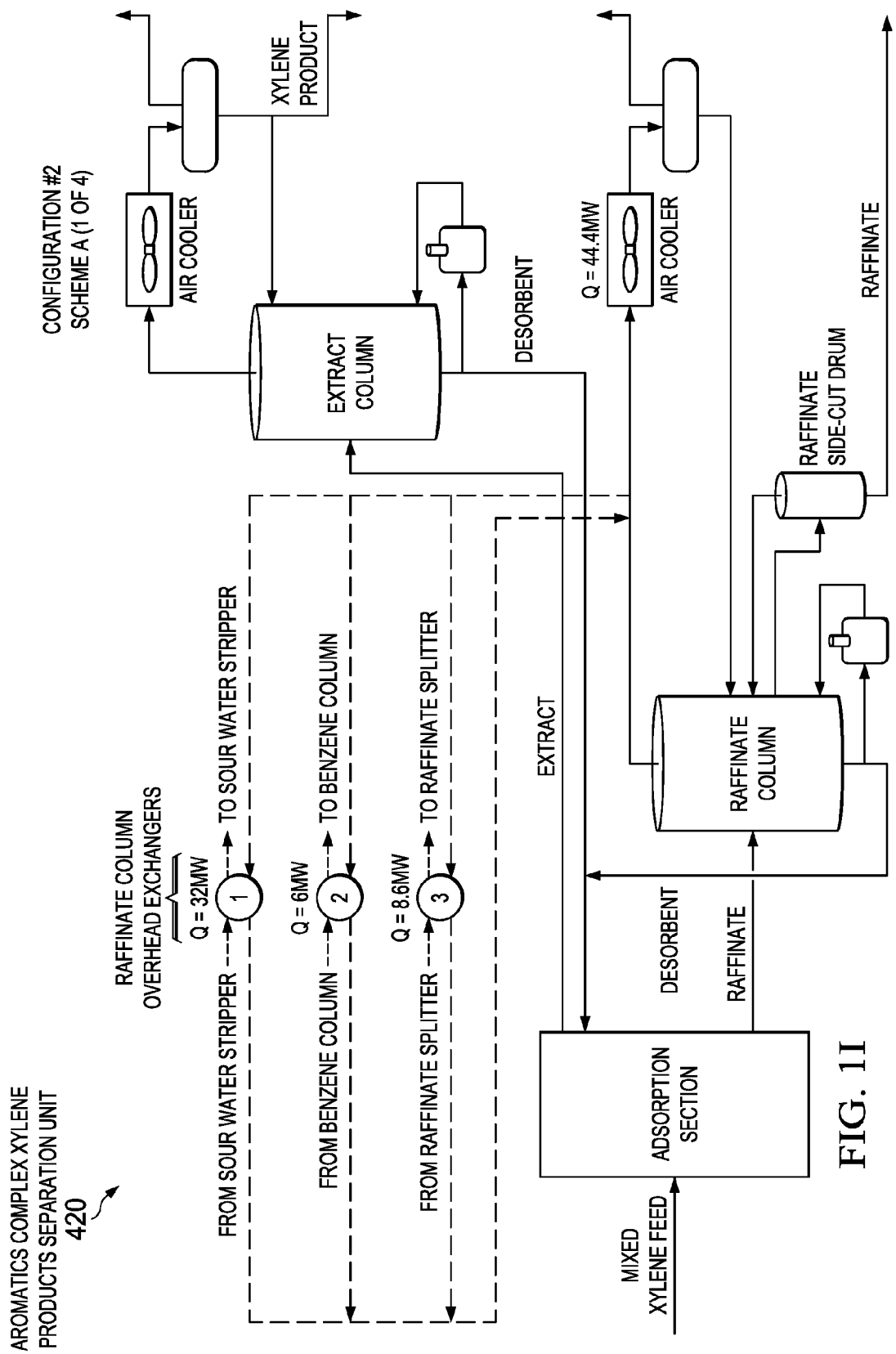
FIG. 1I is a schematic diagram of an aromatics complex xylene products separation unit.

FIG. 1I shows an aromatics complex xylene products separation unit 420 in a crude oil refinery facility. The raffinate overheads column stream can be flowed in the plant as a single stream and split into multiple streams or it can be flowed into the plant as multiple streams. In some implementations, as shown in FIG. 1I, a raffinate column overhead stream is separated into three streams to facilitate heat recovery. A first raffinate overheads stream directly heats a sour water stripper bottoms stream in a first heat exchanger with a thermal duty that can range between about 25 MW and 35 MW (for example, 32 MW). A second raffinate column overheads stream directly heats a benzene column bottoms stream in a second heat exchanger with a thermal duty that can range between about 1 MW and 10 MW (for example, 6 MW). A third raffinate column overheads stream directly heats a raffinate splitter column bottoms stream in a third heat exchanger with a thermal duty that can range between about 5 MW and 15 MW (for example, 8.6 MW). In this manner, the first heat exchanger, the second heat exchanger, and the third heat exchanger are coupled in parallel with each other relative to the flow of the raffinate column overheads. For each raffinate column overheads stream, the transfer of heat directly to another process stream captures heat that would have otherwise been discharged to the environment. The raffinate overhead streams are recombined and are returned to the xylene products separation unit 420 for further processing.

FIG. 1J shows the sour water stripper plant 410 in the crude oil refinery facility. The heated sour water stripper bottoms stream is flowed to the sour water stripper plant 410. As shown in FIG. 1J, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1K:
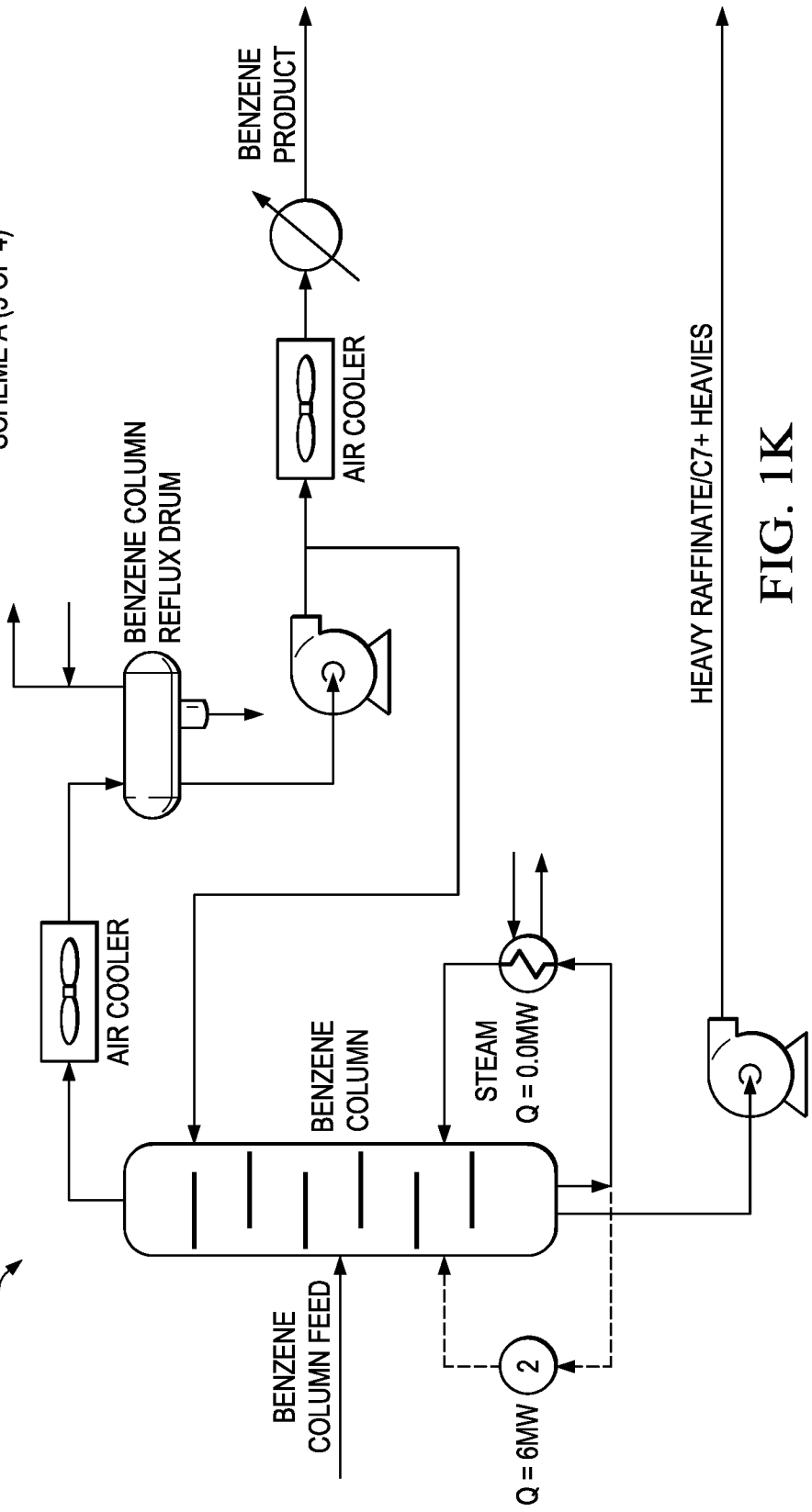
FIG. 1K is a schematic diagram of an aromatics complex benzene products separation unit.

FIG. 1K shows the benzene extraction unit 418 in the crude oil refinery facility. The heated benzene column bottom stream is flowed to the benzene extraction unit 418. As shown in FIG. 1K, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1L:
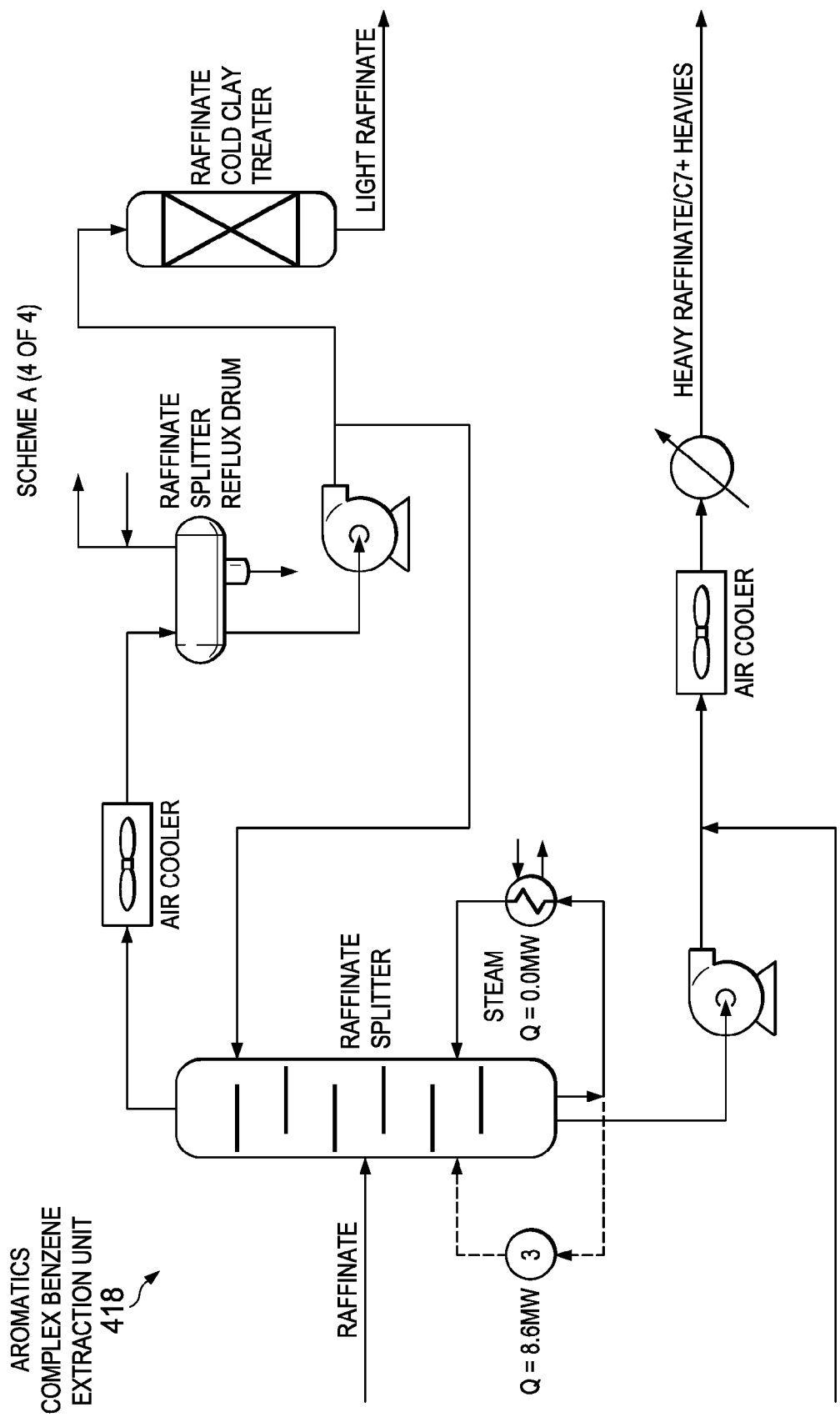
FIG. 1L is schematic diagram of an aromatics complex benzene products separation unit.

FIG. 1L also shows the benzene extraction unit 418 in the crude oil refinery facility. The heated raffinate splitter column bottom stream is flowed to the benzene extraction unit 418. As shown in FIG. 1L, the steam heat input for the raffinate splitter column can be 0 MW because the alternative flow path disclosed in this configuration may satisfy the entire heat load for the operation of the column. In an alternative embodiment, the steam heat input for the raffinate splitter column can be reduced because the alternative flow path disclosed in this configuration may partially satisfy the heat load for the operation of the column.

In this manner, the aromatics complex xylene products separation unit directly heats both the sour water stripper plant and the aromatics complex benzene extraction unit using recovered waste heat, saving about 47 MW of heat energy.

Configuration 2—Scheme B

As shown in FIGS. 1M-1P, in some implementations, multiple first streams in a multiple first plants can be heated indirectly using a second stream in a single second plant. In some implementations, the multiple first plants can include a sour water stripper plant and an aromatics complex benzene extraction unit, and the multiple first streams include a sour water stripper regenerator bottoms, a benzene column bottoms, and a raffinate splitter bottoms streams. The second plant can include an aromatics complex xylene products separation unit, and the second stream can include a raffinate column overheads stream.

The thermal integration described and illustrated in FIGS. 1M-1P can reduce the crude oil refining facility's energy consumption (for example, heating and cooling utilities). For example, a decrease in energy consumption by about 47 MW, for example, 46.6 MW, can translate to about 7% of the energy consumption in the crude oil refining facility. As described later, the heat exchange between process streams can be implemented using an intermediate buffer fluid, for example, water, oil, or other buffer fluid.

Figure 1M:
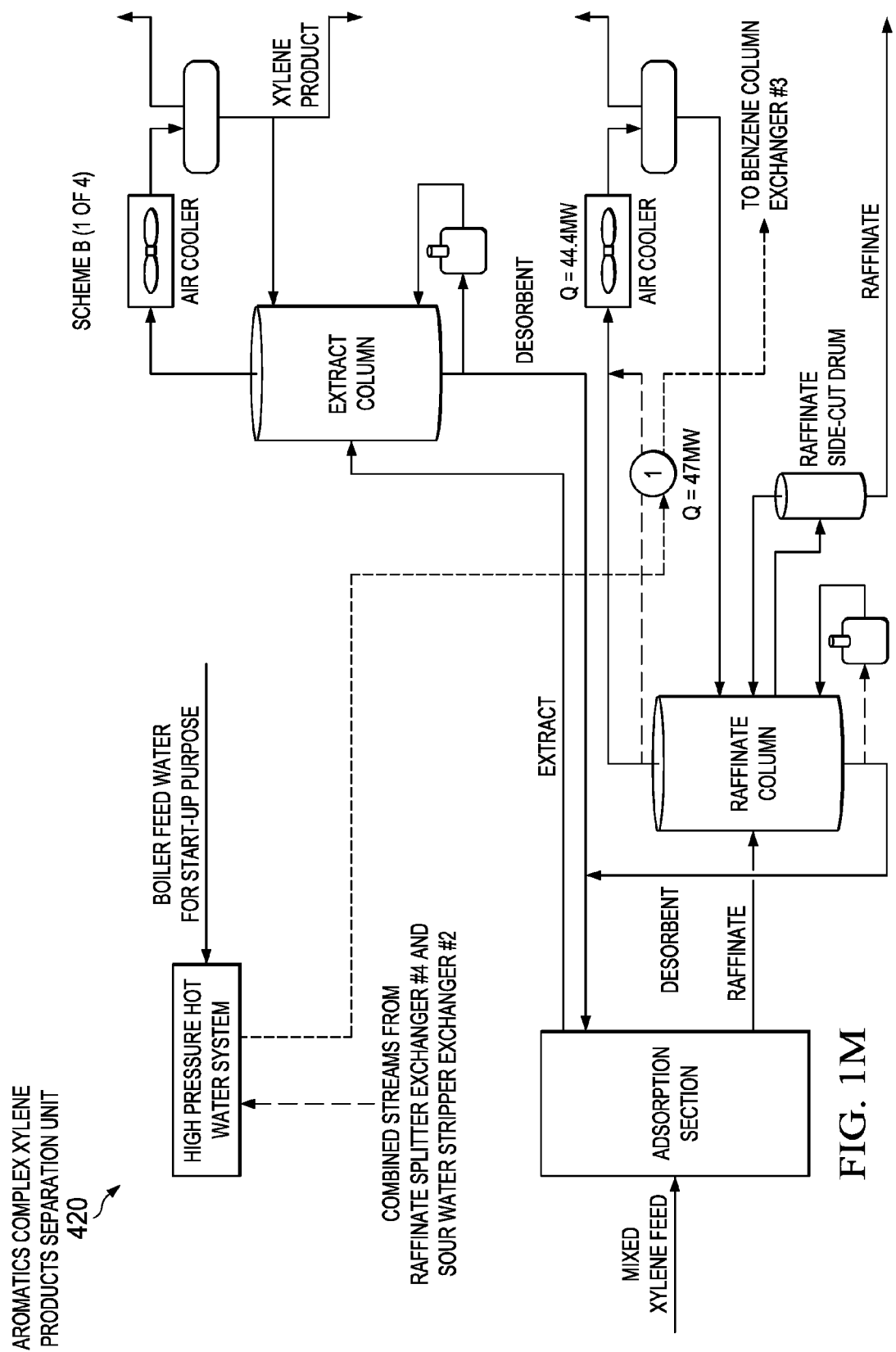
FIG. 1M is a schematic diagram of an aromatics complex xylene products separation unit.

Indirectly heating the streams can include heating the streams through a buffer fluid, for example, oil, water, or other buffer fluid. A buffer fluid (for example, high pressure water) from a buffer fluid tank (for example, hot water tank) is flowed to the aromatics complex xylene products separation unit 420, as shown in FIG. 1M. The buffer fluid can be flowed into a plant as a single stream and split into multiple streams or it can be flowed into a plant as multiple streams.

FIG. 1M shows an aromatics complex xylene products separation unit 420. In some implementations, a buffer fluid from a buffer fluid collection tank is flowed to the aromatics plant xylene products separation unit 420. A raffinate column overheads stream heats the buffer fluid in a first heat exchanger with a thermal duty that can range between about 40 MW and 50 MW (for example, 47 MW). The transfer of heat from the process stream into the buffer fluid captures heat that would have otherwise been discharged to the environment. The raffinate column overheads stream is returned to the xylene products separation unit 420 for further processing.

The heated buffer fluid is flowed to a heated buffer fluid collection header. The heated buffer fluid from the collection header (or in some embodiments, a heated or insulated buffer fluid tank or storage unit that can hold heated collected buffer fluid for a period before use) can be flowed to the sour water striper plant 410 or the benzene extraction unit 418.

Figure 1N:
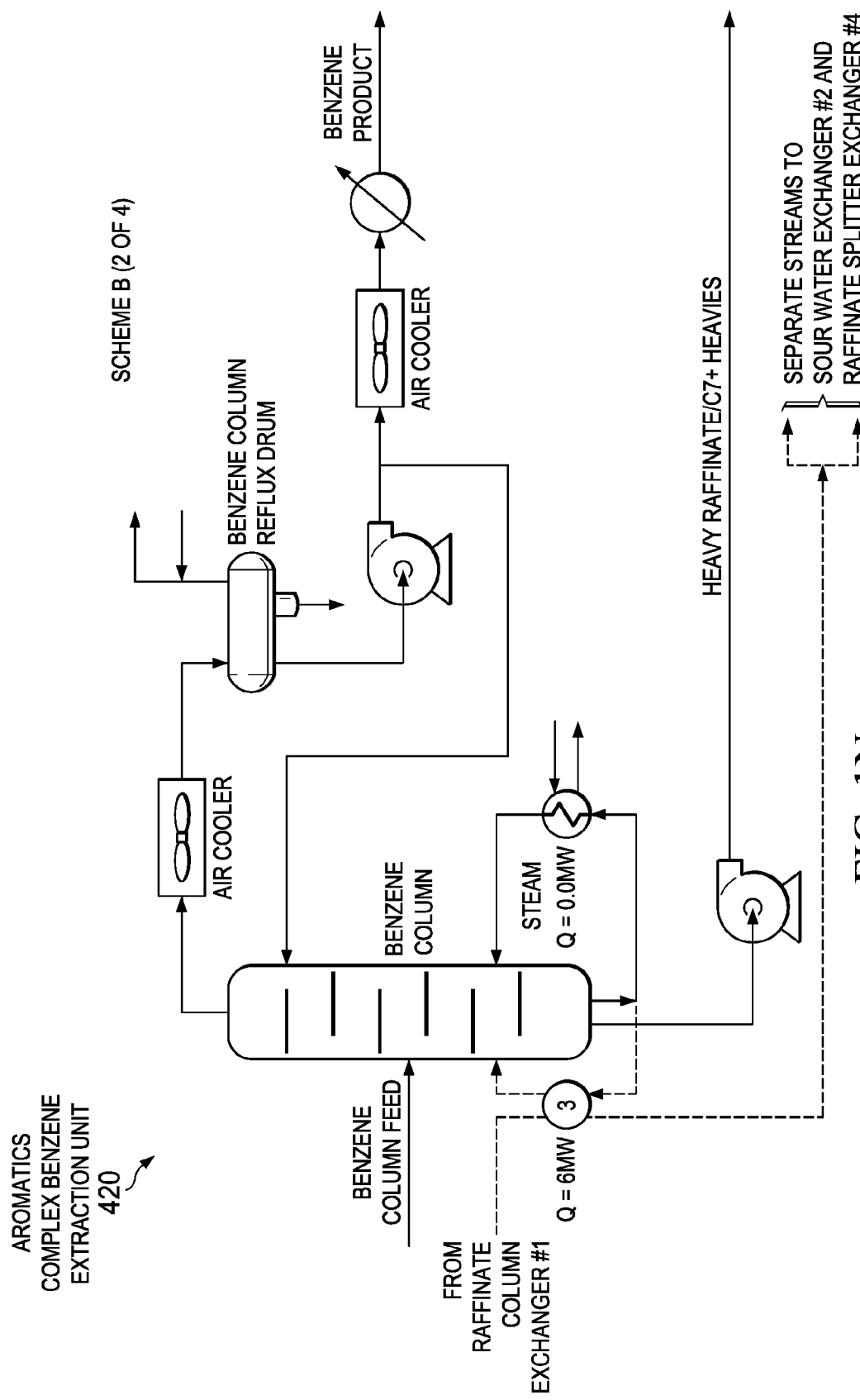
FIG. 1N is a schematic diagram of an aromatics complex benzene products separation unit.

In this instance, the heated buffer fluid exiting the first heat exchanger is flowed to the benzene extraction unit 418. FIG. 1N shows the aromatics complex benzene extraction unit 420 in a crude oil refinery facility. The heated buffer fluid heats a benzene column bottoms stream in a third heat exchanger with a thermal duty that can range between about 1 MW and 10 MW (for example, 6 MW). The third heat exchanger is coupled in series with and is downstream of the first heat exchanger relative to the flow of heated buffer fluid. As shown in FIG. 1N, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1O:
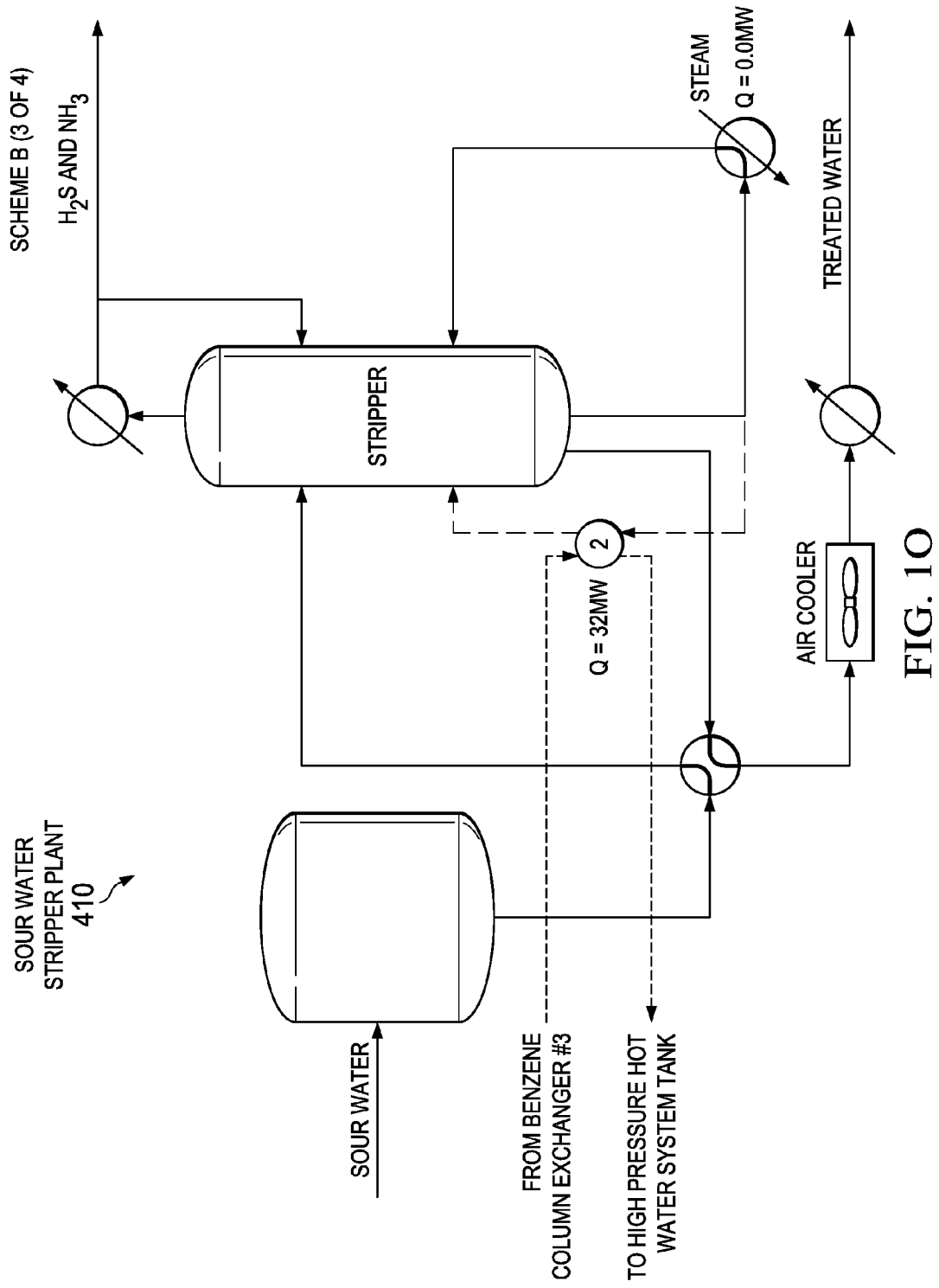
FIG. 1O is a schematic diagram of a sour water stripper plant.

The heated buffer fluid exiting the third heat exchanger is split into two heated buffer fluid streams. FIG. 1O shows the sour water stripper plant 410 in a crude oil refinery facility. A first heated buffer fluid stream is flowed to the sour water stripper plant 410. The first heated buffer fluid stream heats a sour water stripper bottom stream in a second heat exchanger with a thermal duty that can range between about 15 MW and 25 MW (for example, 21 MW). The second heat exchanger is coupled in series with and is downstream of the first heat exchanger relative to the flow of heated buffer fluid. As shown in FIG. 1O, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1P:
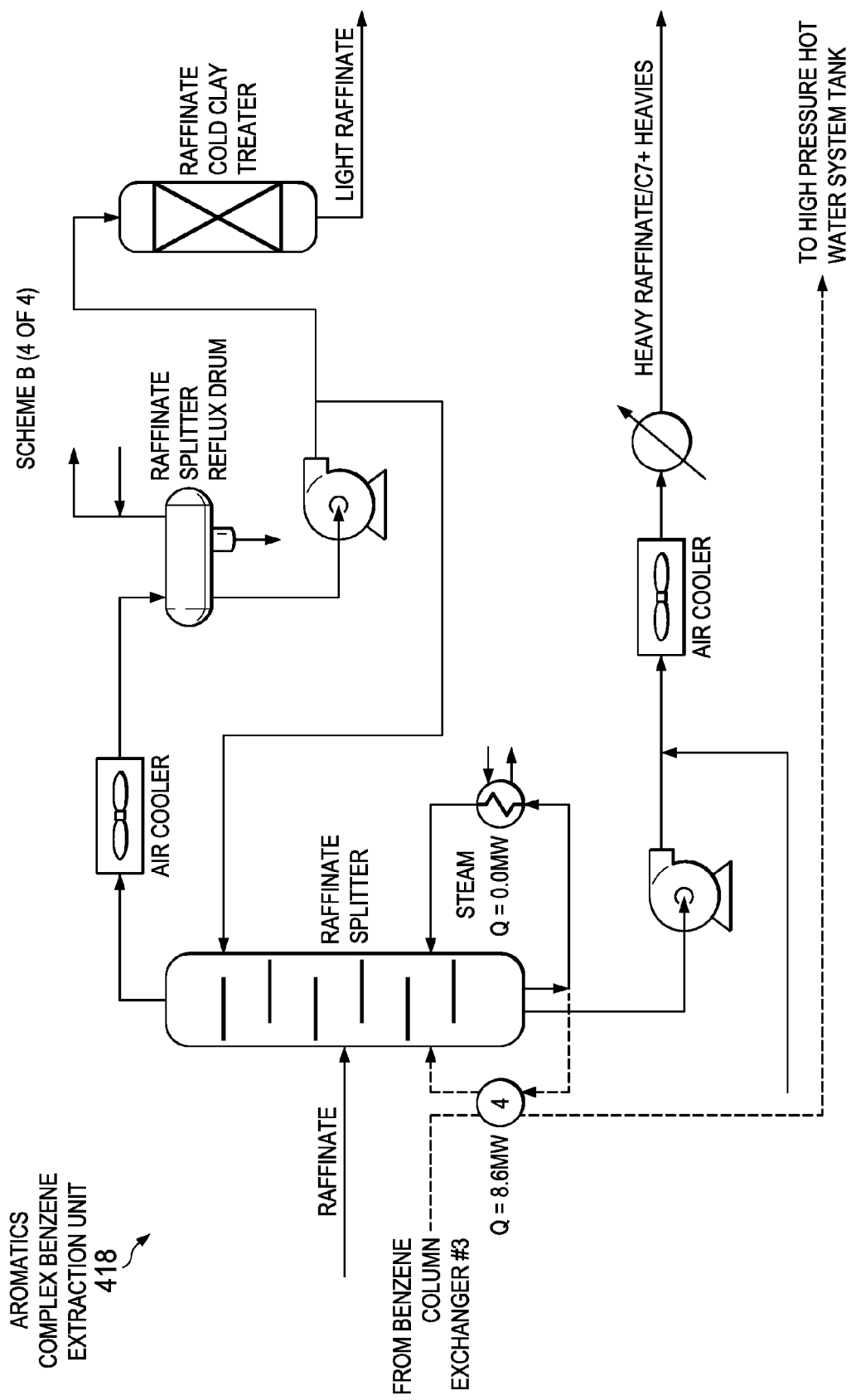
FIG. 1P is a schematic diagram of an aromatics complex benzene products separation unit.

FIG. 1P also shows the aromatics complex benzene extraction unit 420 in a crude oil refinery facility. A second heated buffer fluid stream is flowed to the aromatics complex benzene extraction unit 418. The second heated buffer fluid stream heats a raffinate splitter column bottoms stream in a fourth heat exchanger with a thermal duty that can range between about 5 MW and 15 MW (for example, 8.6 MW). The fourth heat exchanger is coupled in series with and is downstream of the first heat exchanger relative to the flow of heated buffer fluid. As shown in FIG. 1P, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

The heated buffer fluid branches exiting the second heat exchanger and the fourth heat exchanger each flow to the collection header or the buffer fluid tank. In this manner, the second heat exchanger and the fourth heat exchanger are fluidically coupled to each other in parallel relative to the flow of the heated buffer fluid.

In some implementations, the combined heated buffer fluid can be flowed in series through the different plants. For example, the combined heated buffer fluid is flowed first through the combination of the benzene extraction unit and the sulfur recovery plant, and then combined to flow through the benzene extraction unit. The heated buffer fluid exiting the final heat exchanger(s) in this series can then be flowed to the buffer fluid tank. The buffer fluid from the buffer fluid tank can then be flowed to the different plants to restart the waste heat recovery and reuse cycle.

FIGS. 1M-1P show that such recovery and reuse of waste heat indirectly from a first aromatics complex sub-unit can result in decreasing or eliminating the heat energy requirement to heat the streams in both the sour water stripper plant and a second aromatics complex sub-unit such as by about 47 MW.

Configuration 3

Figure 1Q:
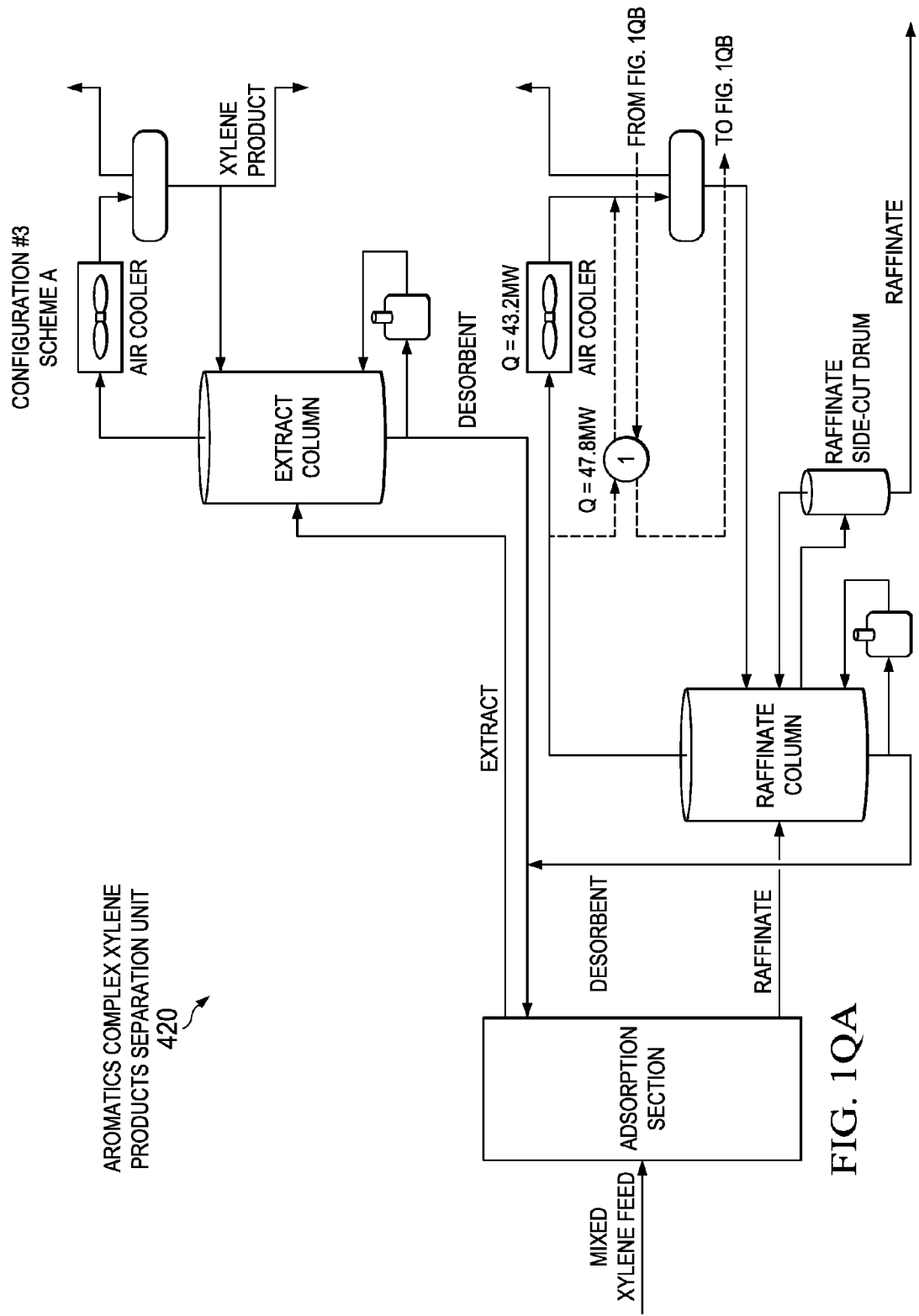
FIG. 1QA is a schematic diagram of an aromatics complex xylene products separation unit.
Figure 1Q:
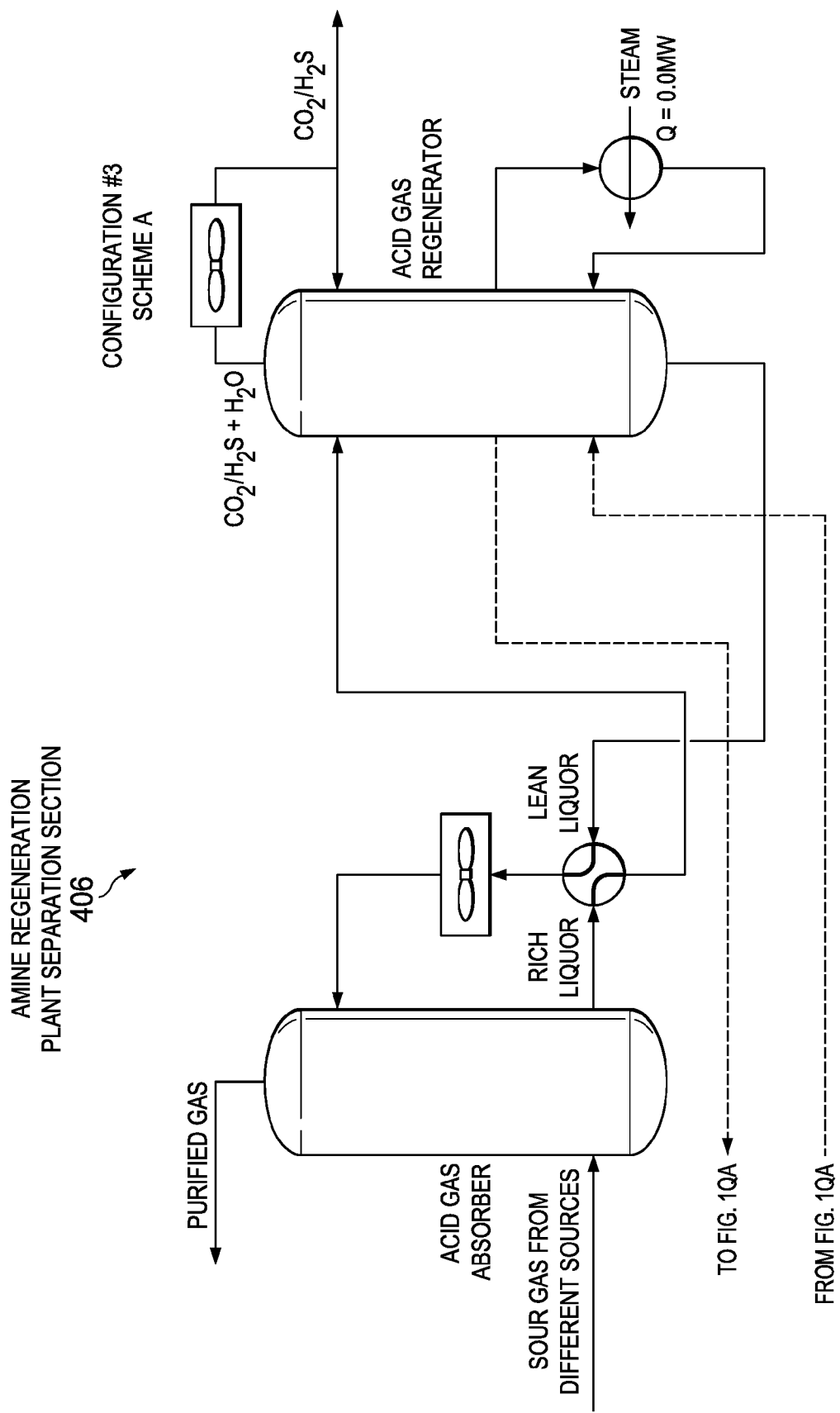

FIGS. 1QA-1RB illustrate configurations and related scheme details for thermally integrating refining an aromatics complex sub-unit with other aromatics complex sub-units and an amine regeneration plant in the crude oil refinery. In certain schemes, a process stream (for example, an acid gas recovery plant stream or other process streams) can be used to directly heat another process stream (for example, an aromatics plant stream or other process stream). In certain configurations, heat exchange between process streams can be implemented using an intermediate buffer fluid, for example, water, oil, or other buffer fluid.

Configuration 3—Scheme A

FIG. 1Q (consisting of FIGS. 1QA and 1QB) illustrates configurations and related scheme details for thermally integrating different refining plants in the crude oil refining facility. The thermal integration described in these configurations and illustrated in FIG. 1Q can reduce the crude oil refining facility's energy consumption (for example, heating and cooling utilities). For example, a reduction in energy consumption by about 48 MW (for example, 47.8 MW), which can translate to at least about 7% of the energy consumption in the crude oil refining facility. As described later, in certain schemes, a process stream (for example, an aromatics complex xylene products unit stream or other process streams) can be used to directly heat another process (for example, an acid gas regenerator or other process stream).

In some implementations, a first stream in a first plant can be directly heated using a second stream in a single second plant. In some implementations, the first plant can include an amine regeneration plant, and the first stream is the acid gas regenerator bottoms stream. The second plant can include an aromatics complex xylene products separation unit, and the second stream can include a raffinate column overheads stream.

FIG. 1QA shows an aromatics complex xylene products separation unit 420 in a crude oil refinery facility. The raffinate overhead stream directly heats an acid gas regenerator bottom stream in a first heat exchanger with a thermal duty that can range between about 45 MW and 55 MW (for example, 47.8 MW). The transfer of heat directly to another process stream captures heat that would have otherwise been discharged to the environment. The raffinate overhead stream is returned to the xylene products separation unit 420 for further processing.

FIG. 1QB shows an amine regeneration plant 406 in a crude oil refinery facility. The heated acid gas regenerator bottoms stream is flowed to the amine regeneration plant 406. As shown in FIG. 1QB, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

In this manner, aromatics complex xylene products separation unit directly heats the amine regeneration plant using recovered waste heat, saving about 48 MW of heat energy.

Configuration 3—Scheme B

Figure 1R:
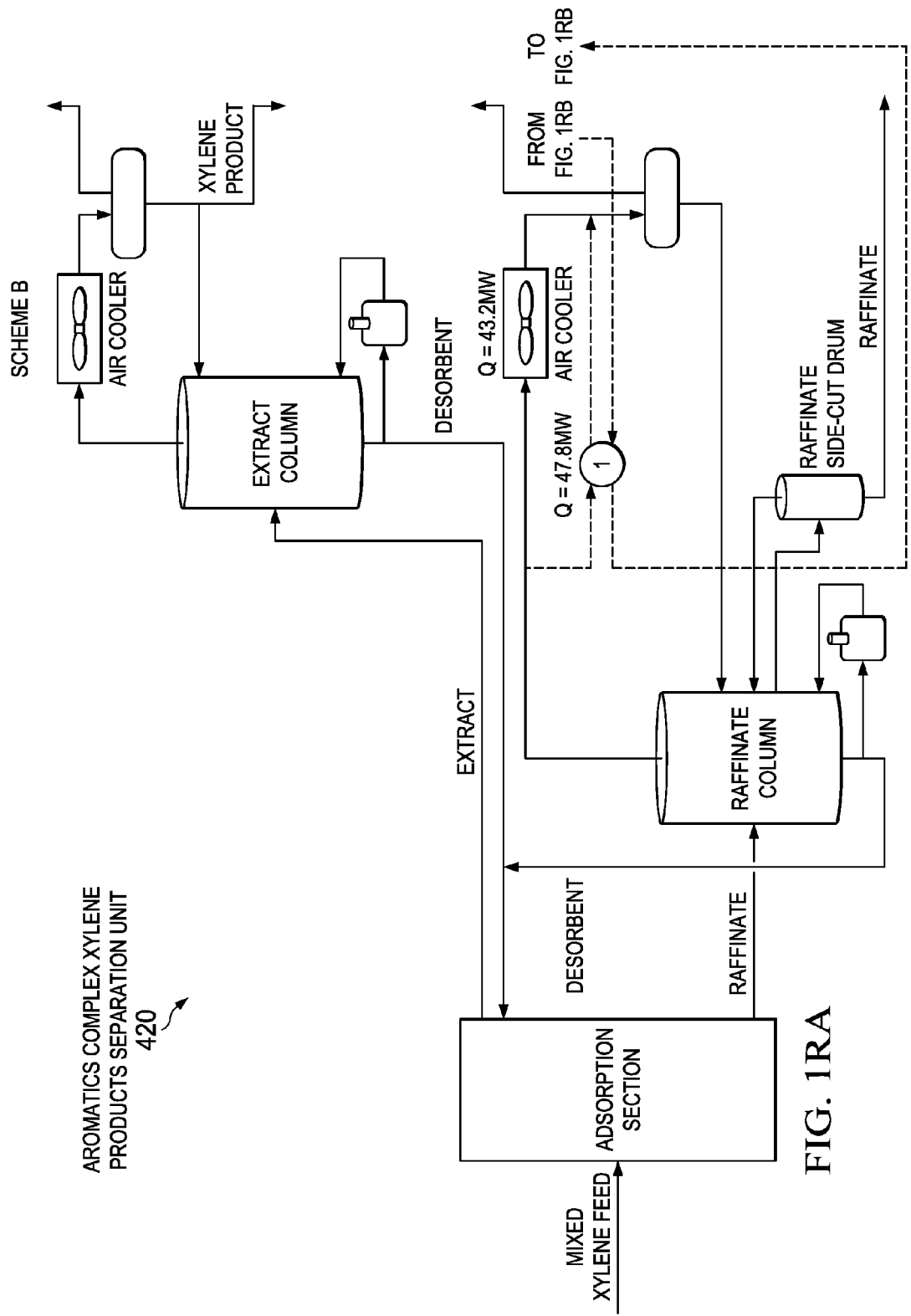
Figure 1R:
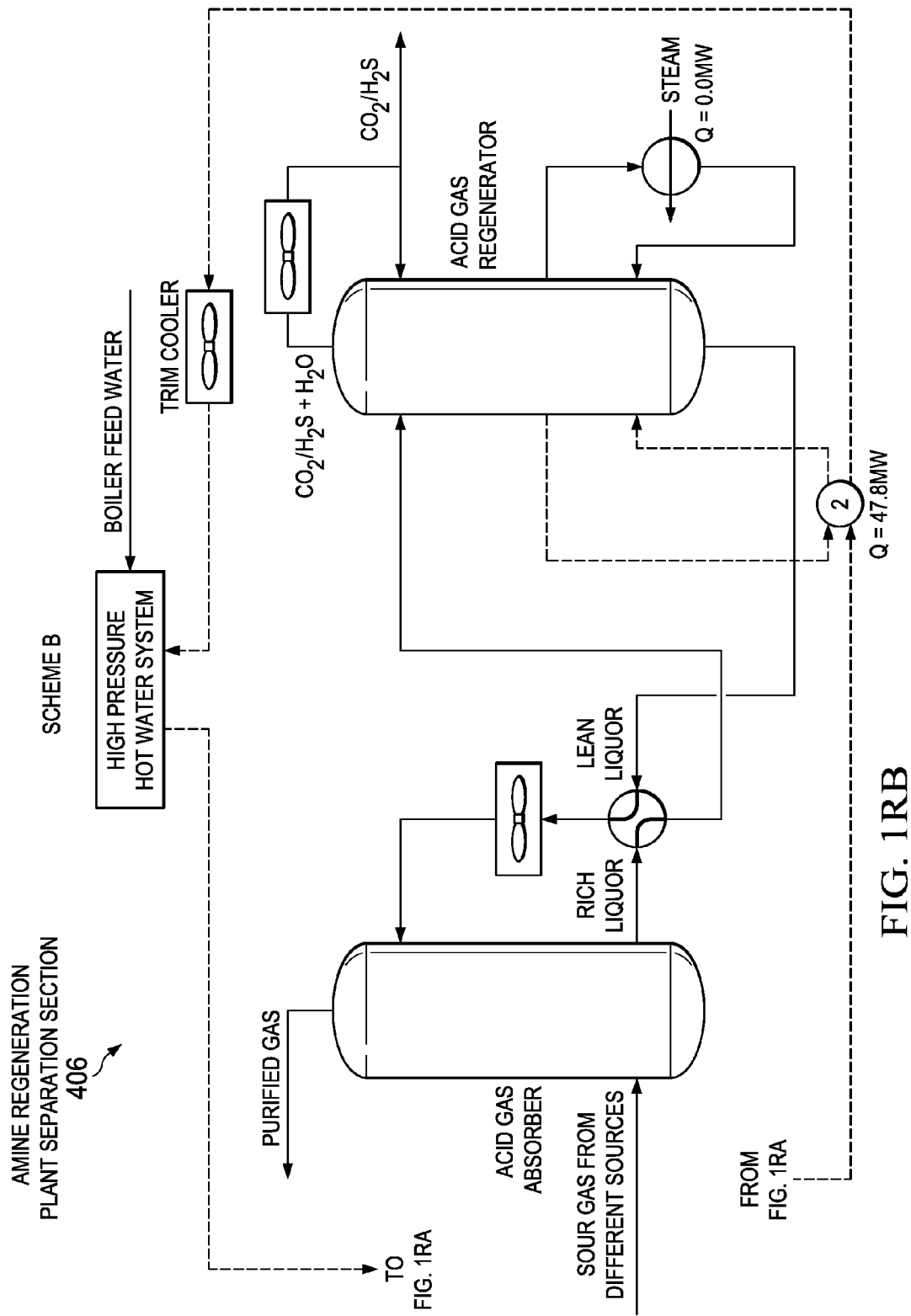

As shown in FIG. 1R (consisting of FIGS. 1RA and 1RB), in some implementations, a first stream in a single first plant can be heated indirectly using a second stream in a single second plant. In some implementations, the first plant can include an amine regeneration plant, and the first stream is the acid gas regenerator bottoms stream. The second plant can include an aromatics complex xylene products separation unit, and the second stream can include a raffinate column overheads stream.

The thermal integration described in these configurations and illustrated in FIG. 1R can reduce the crude oil refining facility's energy consumption (for example, heating and cooling utilities). For example, a reduction in energy consumption by about 48 MW (for example, 47.8 MW) can translate to at least about 7% of the energy consumption in the crude oil refining facility. As described later, the heat exchange between process streams can be implemented using an intermediate buffer fluid, for example, water, oil, or other buffer fluid.

Indirectly heating the streams can include heating the streams through a buffer fluid, for example, oil, water, or other buffer fluid. A buffer fluid (for example, high pressure water) from a buffer fluid tank (for example, hot water tank) is flowed to the aromatics complex xylene products separation unit 420, as shown in FIG. 1R. The buffer fluid can be flowed into a plant as a single stream and split into multiple streams or it can be flowed into a plant as multiple streams.

FIG. 1RA shows an aromatics complex xylene products separation unit 420. A buffer fluid from a buffer fluid collection tank (shown in FIG. 1RB) is flowed to the aromatics plant xylene products separation unit 420 (shown in FIG. 1RA). A raffinate column overheads stream heats the buffer fluid in a first heat exchanger with a thermal duty that can range between about 45 MW and 55 MW (for example, 47.8 MW). The transfer of heat from the process stream into the buffer fluid captures heat that would have otherwise been discharged to the environment. The raffinate column overheads stream is returned to the xylene products separation unit 420 for further processing.

The heated buffer fluid is flowed to a heated buffer fluid collection header. The heated buffer fluid from the collection header (or in some embodiments, a heated or insulated buffer fluid tank or storage unit that can hold heated collected buffer fluid for a period before use) that exited the first heat exchanger is flowed to the amine regeneration plant 406.

FIG. 1RB shows the amine regeneration plant 406 in a crude oil refinery facility. The heated buffer fluid flowed to the amine regeneration plant 406 heats the acid gas regenerator bottoms stream in a second heat exchanger with a thermal duty that can range between about 45 MW and 55 MW (for example, 47.8 MW). The first heat exchanger and the second heat exchanger is coupled with and is downstream of the first heat exchanger relative to the flow of the buffer fluid. As shown in FIG. 1RB, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The buffer fluid exiting the second heat exchanger is flowed back to a buffer fluid tank or collection header where the buffer fluid can be reused and repeat the heating cycle.

FIGS. 1RA-1RB show that such recovery and reuse of waste heat indirectly from an aromatics complex sub-unit can result in decreasing or eliminating the heat energy requirement to heat the streams in the amine regeneration plant such as by about 48 MW In summary, this disclosure describes configurations and related processing schemes of intra-power plants waste heat recovery schemes and plants' thermal coupling for thermal energy consumption reduction in integrated refining-petrochemical facilities synthesized for grassroots medium grade crude oil semi-conversion refineries to increase energy efficiency from specific portions of low grade waste heat sources. The disclosure also describes configurations and related processing schemes of specific intra-plants waste heat recovery schemes and plants' thermal coupling for thermal energy consumption reduction in integrated refining-petrochemical facilities synthesized for integrated medium grade crude oil semi-conversion refineries and aromatics complex for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A method implemented in a crude oil refining facility, the method comprising:
   in a crude oil refining facility comprising a plurality of oil refining plants, each oil refining plant configured to perform at least one oil refining process, wherein a plurality of streams at respective temperatures flow between the plurality of oil refining plants:
   flowing multiple streams, each stream from a sub-unit of a plurality of aromatics plant sub-units included in an aromatics plant of the plurality of oil refining plants, to one or more heat exchangers, wherein a stream from the aromatics plant comprises at least one of benzene, toluene or xylene;
   flowing a stream from a first oil refining plant of the plurality of oil refining plants, the first oil refining plant being different from the aromatics plant, to the one or more heat exchangers, wherein the one or more heat exchangers transfer heat from one or more of the multiple streams to the stream from the first oil refining plant; and
   utilizing the stream from the first oil refining plant heated by one or more of the multiple streams in an oil refining process at the first oil refining plant,
   wherein the one or more aromatics plant sub-units comprises an aromatics complex xylene products separation unit and an aromatics complex benzene extraction plant, and wherein the first oil refining plant comprises a sulfur recovery plant,
   wherein a stream of the multiple streams comprises an raffinate overhead stream in the aromatics complex xylene products separation unit,
   wherein the stream from the first oil refining plant comprises at least one of an amine regenerator bottoms stream in a sulfur recovery plant of the plurality of oil refining plants, a benzene column bottoms stream in an aromatics complex benzene extraction plant of the plurality of aromatics plant sub-units, or a raffinate splitter column bottoms stream in the aromatics complex benzene extraction plant.

2. The method of claim 1, wherein heating the stream from the first oil refining plant comprises directly heating the stream from the first oil refining plant using the multiple streams from the plurality of aromatics plant sub-units.

3. The method of claim 2, wherein directly heating the stream from the first oil refining plant comprises:
   heating, in a first heat exchanger, the amine regenerator bottoms stream in the sulfur recovery plant of the plurality of oil refining plants using a first branch of the raffinate overhead stream;
   heating, in a second heat exchanger, the benzene column bottoms stream in the aromatics complex benzene extraction plant of the plurality of aromatics plant sub-units using a second branch of the raffinate overhead stream;
   heating, in a third heat exchanger, the raffinate splitter column bottoms stream in the aromatics complex benzene extraction plant using a third branch of the raffinate overhead stream;
   flowing the heated amine regenerator bottoms stream to the sulfur recovery plant; and
   flowing the heated benzene column bottoms stream and the heated raffinate splitter column bottoms stream to the aromatics plant.

4. The method of claim 3, wherein the first heat exchanger, the second heat exchanger and the third heat exchanger are fluidically coupled to each other in parallel.

5. The method of claim 2, wherein the plurality of aromatics plant sub-units comprises an aromatics complex xylene products separation unit and an aromatics complex benzene extraction plant, wherein the first oil refining plant comprises a sour water stripper plant in the crude oil facility and wherein directly heating the stream comprises:
   heating, in a first heat exchanger, a sour water stripper bottom stream in the sour water stripper plant using a first branch of the raffinate overhead stream;
   heating, in a second heat exchanger, a benzene column bottoms stream in the aromatics complex benzene extraction plant using a second branch of the raffinate overhead stream; and
   heating, in a third heat exchanger, raffinate splitter column bottoms stream in the aromatics complex benzene extraction plant using a third branch of the raffinate overhead stream; and
   flowing the heated sour water stripper bottom stream, the heated benzene column bottoms stream and the heated raffinate splitter column bottoms stream to the aromatics plant.

6. The method of claim 5, wherein the first heat exchanger, the second heat exchanger and the third heat exchanger are fluidically coupled to each other in parallel.

7. The method of claim 1, wherein heating the stream from the first oil refining plant comprises indirectly heating the stream from the first oil refining plant through a buffer fluid using the multiple streams from the plurality of aromatics plant sub-units.

8. The method of claim 7, wherein the buffer fluid comprises at least one of oil or water.

9. The method of claim 7, wherein indirectly heating the stream from the first oil refining plant using the multiple streams from the plurality of aromatics plant sub-units comprises:
   heating, in a first heat exchanger, the buffer fluid using a raffinate overhead stream in the aromatics complex xylene products separation unit of the plurality of aromatics plant sub-units.

10. The method of claim 9, further comprising:
    flowing the heated buffer fluid to a collection header;
    splitting the heated buffer fluid into a first branch, a second branch and a third branch of the heated buffer fluid;
    flowing the first branch of the heated buffer fluid to a sulfur recovery plant;
    heating, in a second heat exchanger, an amine regenerator bottoms stream in the sulfur recovery plant using the first branch of the heated buffer fluid;
    flowing the second branch of the heated buffer fluid to an aromatics complex benzene extraction unit; and
    heating, in a third heat exchanger, a benzene column bottoms stream in the aromatics complex benzene extraction unit using the second branch of the heated buffer fluid.

11. The method of claim 10, wherein the first heat exchanger and the second heat exchanger are fluidically coupled to each other in series, wherein the first heat exchanger and the third heat exchanger are fluidically coupled to each other in series, wherein the second heat exchanger and the third heat exchanger are fluidically coupled to each other in parallel, wherein the first heat exchanger and the fourth heat exchanger are fluidically coupled to each other in series, wherein the fourth heat exchanger and a combination of the second heat exchanger and the third heat exchanger are fluidically coupled to each other in parallel.

12. The method of claim 10, further comprising:
flowing the heated buffer fluid to an amine regeneration plant separation section; and
heating, in a second heat exchanger, an acid gas regenerator bottom stream in the amine regeneration plant separation section using the heated buffer fluid.

13. The method of claim 12, wherein the first heat exchanger and the second heat exchanger are fluidically coupled to each other in series.

14. The method of claim 9, further comprising:
flowing the heated buffer fluid to an aromatics complex benzene extraction unit; and
heating, in a third heat exchanger, a benzene column bottoms stream in the aromatics complex benzene extraction unit using the heated buffer fluid.

15. The method of claim 14, further comprising:
splitting the heated buffer fluid exiting the third heat exchanger into a first branch and a second branch of the heated buffer fluid;
flowing the first branch of the heated buffer fluid to a sour water stripper plant;
heating, in a second heat exchanger, a sour water stripper bottom stream in the sour water stripper plant using the first branch of the heated buffer fluid;
flowing the second branch of the heated buffer fluid to the aromatics complex benzene extraction unit; and
heating, in a fourth heat exchanger, a raffinate splitter column bottoms stream in the aromatics complex benzene extraction unit using the second branch of the heated buffer fluid.

16. The method of claim 14, wherein the first heat exchanger and the third heat exchanger are fluidically coupled to each other in series, wherein the second heat exchanger and the first exchanger are fluidically coupled to each other in series, wherein the fourth heat exchanger and the third heat exchanger are fluidically coupled to each other in series, wherein the second heat exchanger and the fourth heat exchanger are fluidically coupled to each other in parallel.

17. A method implemented in a crude oil refining facility, the method comprising:
in a crude oil refining facility comprising a plurality of oil refining plants, each oil refining plant configured to perform at least one oil refining process, wherein a plurality of streams at respective temperatures flow between the plurality of oil refining plants:
flowing multiple streams, each stream from a sub-unit of a plurality of aromatics plant sub-units included in an aromatics plant of the plurality of oil refining plants, to one or more heat exchangers, wherein a stream from the aromatics plant comprises at least one of benzene, toluene or xylene;
flowing a stream from a first oil refining plant of the plurality of oil refining plants, the first oil refining plant being different from the aromatics plant, to the one or more heat exchangers, wherein the one or more heat exchangers transfer heat from one or more of the multiple streams to the stream from the first oil refining plant; and
utilizing the stream from the first oil refining plant heated by one or more of the multiple streams in an oil refining process at the first oil refining plant,
wherein the stream in the first oil refining plant comprises an acid gas regenerator bottom stream comprising a weak amine salt in an amine regeneration plant separation section, wherein the multiple streams of the multiple aromatics plant sub-units comprise a raffinate overhead stream in the aromatics complex xylene products separation unit, and wherein the method further comprises heating the acid gas regenerator bottom stream directly using the raffinate column overheads stream in a heat exchanger.

18. A method implemented in a crude oil refining facility, the method comprising:
in a crude oil refining facility comprising a plurality of oil refining plants, each oil refining plant configured to perform at least one oil refining process, wherein a plurality of streams at respective temperatures flow between the plurality of oil refining plants:
flowing multiple streams, each stream from a sub-unit of a plurality of aromatics plant sub-units included in an aromatics plant of the plurality of oil refining plants, to one or more heat exchangers, wherein a stream from the aromatics plant comprises at least one of benzene, toluene or xylene;
flowing a stream from a first oil refining plant of the plurality of oil refining plants, the first oil refining plant being different from the aromatics plant, to the one or more heat exchangers, wherein the one or more heat exchangers transfer heat from one or more of the multiple streams to the stream from the first oil refining plant; and
utilizing the stream from the first oil refining plant heated by one or more of the multiple streams in an oil refining process at the first oil refining plant,
wherein the stream in the first oil refining plant comprises an amine regeneration plant separation section acid gas regenerator bottom stream in the amine regeneration plant separation section, wherein the multiple streams of the multiple aromatics plant sub-units comprise a raffinate overhead stream in the aromatics complex xylene products separation unit, and wherein the method further comprises:
heating a buffer fluid using the raffinate column overheads stream in a first heat exchanger; and
heating the amine regeneration plant separation section acid gas regenerator bottom stream using the heated buffer fluid stream in a second heat exchanger.

* * * * *